US006127604A

United States Patent [19]
Dale et al.

[11] Patent Number: 6,127,604
[45] Date of Patent: Oct. 3, 2000

[54] INTERGENIC REGIONS OF BANANA BUNCHY TOP VIRUS

[75] Inventors: James Langham Dale, Moggill; Robert Maxwell Harding, Lawnton; Benjamin Dugdale, Milton; Peter Ronald Beetham, Kedron; Gregory John Hafner, Wynnum; Douglas Kenneth Becker, Alderly, all of Australia

[73] Assignee: Queensland University of Technology, Australia

[21] Appl. No.: 08/973,068

[22] PCT Filed: May 31, 1996

[86] PCT No.: PCT/AU96/00335

§ 371 Date: Mar. 12, 1998

§ 102(e) Date: Mar. 12, 1998

[87] PCT Pub. No.: WO96/38554

PCT Pub. Date: Dec. 5, 1996

[30] Foreign Application Priority Data

May 31, 1995 [AU] Australia ................................ PN3285

[51] Int. Cl.[7] .............................. A01H 5/00; C12N 5/14; C12N 15/82

[52] U.S. Cl. ...................... 800/298; 435/320.1; 435/419; 435/468; 536/24.1

[58] Field of Search ............................... 435/69.1, 320.1, 435/418, 468; 536/23.72, 24.1; 800/278, 298

[56] References Cited

PUBLICATIONS

Benfey PN, et al. "The cauliflower mosaic virus 35S promoter: Combinatorial regulation of transcription in plants." Science 250: 959–966, Nov. 1990.

Kim Y, et al. "A 20 nucleotide upstream element is essential for the nopaline synthase (nos) promoter activity." Plant Mol. Biol. 24: 105–117, 1994.

Battraw MJ, et al. "Histochemical analysis of CaMV 35S promoter–β–glucuronidase gene expression in transgenic rice plants." Plant Mol. Biol. 15: 527–538, 1990.

Burns et al., "Evidence that Banana Bunchy Top Virus Has a Multiple Component Genome", Arch Virol (1994) 37:371–380.

Burns et al., "The Genome Organization of Banana Bunchy Top Virus: Analysis of Six ssDNA Components", Journal of General Virology (1995), 76, 1471–1482.

Harding, et al., "Nucleotide Sequence of One Component of the Banana Bunchy Top virus Genome Contains a Putative Replicase Gene", Journal of General Virology (1993), 74, 323–328.

Karen et al., "Evidence for Two Groups of Banana Bunchy Top Virus Isolates", Journal of General Virology, Journal of General Virology (1994), 75, 3541–3546.

*Primary Examiner*—Amy J. Nelson
*Attorney, Agent, or Firm*—Fish & Richardson P.C.

[57] ABSTRACT

The invention relates a DNA molecule which is a partial fragment of an intergenic region of a BBTV component or alternatively which DNA molecule is derived from said intergenic region whereby the DNA molecule is capable of promoting, enhancing, regulating, or modifying transcription of a non-BBTV gene.

11 Claims, 21 Drawing Sheets

```
                    ─────────⇒         ⇐─────────
  1  GGCGCTGGGG CTTATTATTA CCCCCAGCGC CGGGACGGGA CATGGGCTTT TTAAATGGGC
 61  TTTGCGAGTT TGAACAGTTC AGTATCTTCG TTATTGGGCC AACCCGGCCC AATAATTAAG
121  AGAACGTGTT CAAATTCGTG GTATGACCGA AGGTCAAGGT AACCGGTCAA CATTATTCTG
181  GCTTGCGCAG CAAGATACAC GAATTAATTT ATTAATTCGT AGGACACGTG GACGGACCGA
241  AATACTCTTG CATCTCTATA AATACCCTAA TCCTGTCAAG GATAATTGCT CTCTCTCTTC
301  TGTCAAGGTG GTTGTGCTGA GGCGGAAGAT CGCCAGCGGC GATCGTCGGA ACGACCTGCA
361  TCTAGAGAGG CGGCGAGGAA ACTACGAAGC GTATATCGGG TATTTATAGA CTTATAGCGT
421  AGCTAGAAGT ATACACTGTA CAGATATTGT ATCTTGTAAA TTACGAAGCA ATTCGTATTT
481  GATATTAATA AAACAACTGG GTTTGTTAAT GTTTACATTA ACTAGTATCT TATATGTACA
541  AATTAAAATA CAGTATACGG AACGTATACT AACGTAAAAA TTAAATGATA GGCGAAGCAT
601  GATTAACAGG TGTTTAGGTA TAATTAACAT AATTATGAGA AGTAATAATA ATACGGAAAA
661  TGAATAAGTA TGAGGTGAAA GAGGAGATAT TAGAATATTT AAAAACCCAA TTATATTATT
721  TTGGAACGAA ATACAACACG CTATGAAATA CAAGACGCTA TGACAAATGT ACGGGAATAT
781  GATTGTGTAT CTTAACGTAT AAGGGCCGCA GGCCCGTCAA GTTGAATGAA CGGTCCAGAT
841  TAATTCCTTA GCGACGAAGA AAGGAATCTT AAAGGGGACC ACATTAAAGA CAGCTGTCAT
901  TGATTAAATA AATAATATAA TAACCAAAAG ACCTTTGTAC CCTTCCTAAT GATGACGTAT
961  AGGGGTGTCC CGATGTAATT TAACATAGCT CTGAAAAGAG ATATGGGCCG TTGGATGCCT
1021 CCATCGGACG ATGGAGGTTG AATGAACTTC TGCTGACGTA
```

FIG. 1A

```
1    AGCGCTGGGG ACTATTATTA CCCCCAGCGC TCGGGACGGG ACATGGGCTA ATGGATTGTG
                    ⇒              ⇐
61   GATATAGGGC CCAAAGGGCC CGTTTAGATG GGTTTTGGGC TCATGGGCTT TATCCAGAAG

121  ACCAAAAACA GGCGGGAACC GTCCCAAATT CAAACTTCGA TTGCTTGCCC TGCAACGCAT
                                            ∨              ⇓
181  CTAGAAGTCT ATAAATACCA GTGTCTAGAT AGATGTTCAG ACAAGAAATG GCTAGGTATC
                                                  M  F  R   Q  E  M   A  R  Y  P

241  CGAAGAAATC CATCAAGAAG AGGCGGGTTG GGCGCCGGAA GTATGGCAGC AAGGCGGCAA
      K  K  S    I  K  K   R  R  V    G  R  R  K  Y  G  S   K  A  A  T

301  CGAGCCACGA CTACTCGTCG TCAGGGTCAA TATTGGTTCC TGAAAACACC GTCAAGGTAT
      S  H  D   Y  S  S    S  G  S  I  L  V  P   E  N  T    V  K  V  F

361  TTCGGATTGA GCCTACTGAT AAAACATTAC CCAGATATTT TATCTGGAAA ATGTTTATGC
      R  I  E   P  T  D    K  T  L  P  R  Y  F   I  W  K    M  F  M  L

421  TTCTTGTGTG CAAGGTGAAG CCCGGAAGAA TACTTCATTG GGCTATGATC AAGAGTTCTT
      L  V  C   K  V  K    P  G  R  I  L  H  W   A  M  I    K  S  S  W

481  GGGAAATCAA CCAGCCGACA ACCTGTCTGG AAGCCCCAGG TTTATTTATT AAACCTGAAC
      E  I  N   Q  P  T    T  C  L  E  A  P  G   L  F  I    K  P  E  H

541  ACAGCCATCT GGTTAAACTG GTATGTAGTG GGGAACTTGA AGCAGGAGTC GCAACAGGAA
      S  H  L   V  K  L    V  C  S  G  E  L  E   A  G  V    A  T  G  T

601  CATCAGATGT TGAATGTCTT TTGAGGAAGA CAACCGTGTT GAGGAAGAAT GTAACAGAGG
      S  D  V   E  C  L    L  R  K  T  T  V  L   R  K  N    V  T  E  V

661  TGGATTATTT ATATTTGGCA TTCTATTGTA GTTCTGGAGT AAGTATAAAC TACCAGAACA
      D  Y  L   Y  L  A    F  Y  C  S  S  G  V   S  I  N    Y  Q  N  R

721  GAATTACATA TCATGTTTGA TATGTTTATG TAAACATAAA CTATTGTATG GAATGAAATC
      I  T  Y   H  V  *

781  CAAATAACAT ACAACAGCT ATGAATACA AGACGCTATG ACAAAAGTAC TGGTATATGA

841  TTAGGTATCC TAACGATCTA GGGCCGAAGG CCCGTGAGCA ATATGCGTCG AAATAATGTT

901  TAACAAACAA ATATACATGA TACGGATAGT TGAATACATA AACAACGAGG TATACAATAC

961  AACAAACTGT TGTAAAGAAA TAAAAAATAA GAAGAGAGAG TATATTTGTG TCGGATAAGC

1021 ATCACACCCA CCACTTTAGT GGTGGGCCAG ATGTCCCGAG TTAGTGCGCC ACGTA
```

FIG. 1B

```
         ━━━━━━━━━━━⇒        ⇐━━━━━━━━━
  1   AGCGCTGGGG CTTATTATTA CCCCCAGCGC TCGGGACGGG ACATCACGTG CGTCAACAAA
 61   TGCACGTGAC TGATATAAGG GACATAACGG GTTTAGATAA CGGTTTATGC GGATTAGAAT
121   ATAACGTCAC GTGTGAAAGC CGAAAGGCAC GTGACGAAGA CAAATGGATT GAATAAACAT
181   TTGACGTCCG GTAGCTTCCG AAGGAAGTAA GCTTCGCGGC GAAGCAAACC ATTTATATAT
                                          ▽
241   TTGCGTAGGC TTGCGGCCTA TAAATAGGAC GCAGCTAAAT GGCATTAACA ACAGAGCGGG
                                                  M  A  L   T  E  R  V
301   TGAAACTATT CTTTGAATGG TTTCTGTTCT TTGGAGCAAT ATTTATTGCG ATTACAATAT
       K  L  F   F  E  W   F  L  F  F  G  A  I   F  I  A    I  T  I  L
361   TATATATATT GTTGGTTTTG CTCTTTGAGG TACCCAGGTA TATTAAGGAG CTCGTGAGGT
       Y  I  L   L  V  L   L  F  E  V  P  R  Y   I  K  E    L  V  R  C
421   GTTTGGTAGA ATACCTGACC AGACGACGTG TATGGATGCA GAGGACGCAG TTGACGGAGG
       L  V  E   Y  L  T   R  R  R  V  W  M  Q   R  T  Q    L  T  E  A
481   CAACTGGAGA TGTAGAGATC GGCAGAGGTA TTGTGGAAGA CAGACGAGAT CAAGAACCGG
       T  G  D   V  E  I   G  R  G  I  V  E  D   R  R  D    Q  E  P  A
541   CTGTCATACC ACATGTATCT CAGGTAATCC CTTCTCAACC AAATAGAAGG GATGATCAAG
       V  I  P   H  V  S   Q  V  I  P  S  Q  P   N  R  R    D  D  Q  G
601   GAAGACGAGG AAACGCTGGA CCTATGTTCT AATACACGGT ATATTAATAT ACGAAATATA
       R  R  G   N  A  G   P  M  F  *
661   AATGGGTATT GATGTAAATG ATCATACATA ATATATGTAT GATAATGAAA CATATTGTAA
721   TATGTGAATT GTAAACGAGA GTTGTATGTA TAAAACATAC AACACGCTAT GAAATACAAG
781   ACGCTATGAC AAAAGTACTG GTATATGATT AGGTATCCTA ACGATCTAGG GCCGAAGGCC
841   CGTGAGCAAT ATGCGTCGAA ATAATGTTTA ACAAACAAAT ATACATGATA CGGATAGTTG
901   AATACATAAA CAACGAGGTA TACAATACAA CAAACTGTTG TAAAGAAATA AAAAATAAGA
961   AGAGATAGTA TATTTGTGTT GGATAAGCCT TGCAACCACC ACTTTAGTGG TGGGCCAGAT
1021  GTCCCGAGTT AGTGCGCCAC GTA
```

FIG. 1C

```
  1   AGCGCTGGGG CTTATTATTA CCCCCAGCGC TCGGGACGGG ACATCACGTG CAACTAACAG

61   ACGCACGTGA GAATGCAGTA GCTTGCAGCG AAAGATAGAC GTCAACATCA ATAAAGAAGA

121   AGGAATATTC TTTGCTTCGG CACGAAGCAA AGGGTATAGA TATTTGTTCG AGATGCGAAA
                                                                     ▽
181   ATGGAGGCTA TTTAAACCTG ATGGTTTTGT GATTTCCGAA ATCACTCGTC GGAAGAGAAA
                                                                     M

241   TGGAGTTCTG GGAATCGTCT GCCATGCCTG ACGATGTCAA GAGAGAGATT AAGGAAATAT
       E  F  W   E  S  S   A  M  P  D  D  V  K   R  E  I    K  E  I  Y

301   ATTGGGAAGA TCGGAAGAAA CTTCTGTTCT GTCAGAAGTT GAAGAGCTAT GTCAGAAGGA
       W  E  D   R  K  K   L  L  F  C  Q  K  L   K  S  Y    V  R  R  I

361   TTCTTGTTTA TGGAGATCAA GAGGATGCCC TTGCCGGAGT GAAGGATATG AAGACTTCTA
       L  V  Y   G  D  Q   E  D  A  L  A  G  V   K  D  M    K  T  S  I

421   TTATTCGCTA TAGCGAATAC TTGAAGAAAC CATGTGTGGT AATTTGTTGT GTTAGCAATA
       I  R  Y   S  E  Y   L  K  K  P  C  V  V   I  C  C    V  S  N  K

481   AATCAATTGT GTATAGGTTA AACAGCATGG TGTTCTTTTA TCATGAATAC CTTGAAGAAC
       S  I  V   Y  R  L   N  S  M  V  F  F  Y   H  E  Y    L  E  E  L

541   TAGGTGGTGA TTACTCAGTA TATCAAGATC TCTATTGTGA TGAGGTACTC TCTTCTTCAT
       G  G  D   Y  S  V   Y  Q  D  L  Y  C  D   E  V  L    S  S  S  S

601   CGACAGAGGA AGAAGATGTA GGAGTAATAT ATAGGAATGT TATCATGGCA TCGACACAAG
       T  E  E   E  D  V   G  V  I  Y  R  N  V   I  M  A    S  T  Q  E

661   AGAAGTTCTC TTGGAGTGAT TGTCAGCAGA TAGTTATATC AGACTATGAT GTAACATTAC
       K  F  S   W  S  D   C  Q  Q  I  V  I  S   D  Y  D    V  T  L  L

721   TCTAATGTAA TATCCATTAT CATCAATAAA ATAATGGAAT GTTGATTATG TATTTATCAT
       *

781   AAATACATAA TGGTATACGT ATAGCATAAA ATACATTAAC CAACATACAA CACACTATAA

841   AATACAACAC GCTATGACAA ATGTACGGGT ATATGATTGG GTTATATTAA CCCCTTAAGG

901   GCCGAAGGCC CGTTTAAATA TGTGTTGGAC GAAGTCCAAA CACAAAAAAG TAAGCAGAAC

961   AACGGAATAA TATGAGCTGG CAACGTAGGG TCCATGTCCC GAGTTAGTGC GCCACGTA
```

FIG. 1D

```
                  ───────────⇒        ⇐───────────
  1   AGCACGGGGG ACTATTATTA CCCCCCGTGC TCGGGACGGG ACATGACGTC AGCAAGGATT

61   ATAATGGGCT TTTTATTAGC CCATTTATTG AATTGGGCCG GGTTTTGTCA TTTTACAAAA

121   GCCCGGTCCA GGATAAGTAT AATGTCACGT GCCGAATTAA AAGGTTGCTT CGCCACGAAG

181   AAACCTAATT TGAGGTTGCG TATTCAATAC GCTACCGAAT ATCTATTAAT ATGTGAGTCT
                                                      ▽
241   CTGCCGAAAA AAATCAGAGC GAAAGCGGAA GGCAGAAGCG ATGGATTGGG CGGAATCACA
                                                   M   D   W   A   E   S   Q

301   ATTCAAGACC TGTACTCATG GATGCGATTG GAAGAAGATA TCATCGGATT CAGCCGATAA
       F   K   T   C   T   H   G   C   D   W   K   K   I   S   S   D   S   A   D   N

361   TCGACAATAT GTACCATGCG TCGATTCTGG AGCTGGAAGA AAGTCGCCTC GCAAGGTACT
       R   Q   Y   V   P   C   V   D   S   G   A   G   R   K   S   P   R   K   V   L

421   TCTTAGATCT ATTGAAGCTG TGTTTAACGG AAGCTTCAGC GGAAATAATA GGAATGTTCG
       L   R   S   I   E   A   V   F   N   G   S   F   S   G   N   N   R   N   V   R

481   TGGATTTCTC TACGTATCGA TCAGAGACGA TGACGGAGAA ATGCGTCCAG TACTCATAGT
       G   F   L   Y   V   S   I   R   D   D   G   E   M   R   P   V   L   I   V

541   ACCATTCGGA GGATATGGAT ATCATAATGA TTTTTATTAT TTCGAAGGGA AGGGGAAAGT
       P   F   G   G   Y   G   Y   H   N   D   F   Y   Y   F   E   G   K   G   K   V

601   TGAATGTGAT ATATCATCAG ATTATGTTGC GCCAGGAATA GATTGGAGCA GAGACATGGA
       E   C   D   I   S   S   D   Y   V   A   P   G   I   D   W   S   R   D   M   E

661   AGTTAGTATT AGTAACAGCA ACAACTGTAA TGAATTATGT GATCTGAAGT GTTATGTTGT
       V   S   I   S   N   S   N   N   C   N   E   L   C   D   L   K   C   Y   V   V

721   TTGTTCGTTA AGAATCAAGG AATAAAAGTT GTGCTGTAAT GTTAATTAAT AAAACGTATA
       C   S   L   R   I   K   E   *

781   TTTGGGAAAT TGATAGTTGT ATAAAACATA CAACACACTA TGAAATACAA GACGCTATGA

841   CAAATGTACG GGTATCTGAA TGAGTTTTAG TATCGCTTAA GGGCCGCAGG CCCGTTAAAA

901   ATAATAATCG AATTATAAAC GTTAGATAAT AATCAGAGAT AGGTGATCAG ATAATATAAA

961   CATAAACGAA GTATATGCCG GTACAATAAT AAAATAAGTA ATAACAAAAA AAATATGTAT

1021  ACTAATCTCT GATTGGTTCA GGAGAAAGGC CCACCAACTA AAAGGTGGGG AGAATGTCCC

1081  GATGACGTA
```

```
BBTV1  ATGTCCCGAGTTAGTGCGCCAGTTAGGGCTAAGGGCTGGGGCTTATTATTACCCCCAGGCTTCGGGACGGGACAT
BBTV2  .........TGCTG.ACGTAGGCGCTGGGGCTTATTATTACCCCCAGGCC.GGGACGGGACAT
BBTV3  ATGTCCCGAGTTAGTGCGCCAGTTAGGCGCTAAGGCTGGGGCTTATTATTACACCCCAGCGCTCGGGACGGGACAT
BBTV4  ATGTCCCGAGTTAGTGCGCCAGTTAGGCGCTAAGGCTGGGGCTTATTATTACCCCCAGCGCTCGGGACGGGACAT
BBTV5  ATGTCCCGAGTTAGTGCGCCAGTGCGCTAAGGCGCTGGGGCTTATTATTACCCCCAGCGCTCGGGACGGGACAT
BBTV6  ATGTCCCGA.....TG....ACGTAAGCACGGGGACTATTATTACCCCCGTGCTCGGGACGGGACAT
       **          *****  *   *  ** ****  ****  *************  * ** *****************
```

```
BBTV1  GAAATACAACACGCTATGAAA.........CACACTATGACAAAAGTAYGGGTATCTGATTGGGTTATCTTAACGATCT.AGGGCCGTAAGGCCGT
BBTV2  GAAATACAACACGCTATGAAATACAAGACGCTATGACAAAGTAYGGGATGTAYGGGWATMTGATTGTGTA.TCTTAACG.TATAAGGGCGCAGGCCGT
BBTV3  AACATACAACACGCTATGAAATACAAGACGCTATGACAAAAGTACTGGTATATATGATTAGGTA.TCCTAACGATCTA.QGGCCGTAAGGCCCGT
BBTV4  AACATACAACACGCTATGAAATACAAGACGCTATGACAAAAGTACTGGTATATATGATTAGGTA.TCCTAACGATCTA.QGGCCCGTAAGGCCCGT
BBTV5  AACATACAACACACTATGAAATACAACACGCTATAACAAAATGTACGGGTATTGATTGGGCTATATTAACCCCTTAAGGGCCGAAGGCCCGT
BBTV6  AACATACAACACACTATGAAATACAAGACGCTATGACAAATGTACAAATGTACGGGTATCTGAATGAGTTTTAGTA.TCGCTTAAGGGCGCAGGGCCGT
       ******  *** ****  ****        *****  ****   ****  ***  *****  *  **        **             ******
```

FIG. 4

```
           1                                                           50
bbtvpro1   .......... .......... .......... .......... ..........
bbtvpro5   .......... .......... .......... .......... ..........
bbtvpro3   .......... .......... .......... .......... ..........
bbtvpro4   .......... .......... .......... .......... ..........
bbtvpro6   .......... .......... .......... .......... ..........
bbtvpro2   TATACGGAAC GTATACTAAC GTAAAAATTA AATGATAGGC GAAGCATGAT 51                                                          100
bbtvpro1   .......... .......... .......... .......... ..........
bbtvpro5   .......... .......... .......... .......... ..........
bbtvpro3   .......... .......... .......... .......... ..........
bbtvpro4   ...TACACGG TATATTAATA TACGAAATAT AAATGGGTAT TGATGTAAAT
bbtvpro6   .......... .......... .......... .......... ..........
bbtvpro2   TAACAGGTGT TTAGGTATAA TTAACATAAT TATGAGAAGT AATAATAATA 101                                                         150
bbtvpro1   .......... .......... .......... .......... ..........
bbtvpro5   .......... .......... .......... .......... ..........
bbtvpro3   .......... .......... .........T ATGTTTATGT AAACATAAAC
bbtvpro4   GATCATACAT AATATATGTA TGATAATGAA ACATATTGTA ATATGTGAAT
bbtvpro6   .......... .....AAGTT GTGCTGTAAT GTTAATTAAT AAAACGTATA
bbtvpro2   CGGAAAATGA ATAAGTATGA GGTGAAAGAG GAGATATTAG AATATTTAAA 151                                                         200
bbtvpro1   .......... .......... .......... .......... ..........
bbtvpro5   .......... .......... ...TGTAATA TCCATTATCA TCAATAAAAT
bbtvpro3   TATTGTATGG AATGAAATCC AAATAACATA CAACACGCTA TGAAATACAA
bbtvpro4   TGTAAACGAG AGTTGTATGT ATAAAACATA CAACACGCTA TGAAATACAA
bbtvpro6   TTTGGGAAAT TGATAGTTGT ATAAAACATA CAACACACTA TGAAATACAA
bbtvpro2   AACCCAATTA TATTATTTTG GAACGAAATA CAACACGCTA TGAAATACAA
```

FIG. 11A

```
         201                                                    250
bbtvpro1  .......... .......... .......... .......... ..........
bbtvpro5  AATGGAATGT TGATTATGTA TTTATCATAA ATACATAATG GTATACGTAT
bbtvpro3  GACGCTATGA CAAAAGTACT GGTATATG.A TTAGGTATCC TAACGATCTA
bbtvpro4  GACGCTATGA CAAAAGTACT GGTATATG.A TTAGGTATCC TAACGATCTA
bbtvpro6  GACGCTATGA CAAATGTACG GGTATCTGAA TGAGTTTTAG TATCGCTTAA
bbtvpro2  GACGCTATGA CAAATGTACG GGAATATG.A TTGTGTATCT TAACGTATAA 251                                                    300
bbtvpro1  .........A CAAGTAATGA CTTTACAGCG CACGCTCC.. ..........
bbtvpro5  AGCATAAAAT ACATTAACCA ACATACAACA CACTATAA.. ..........
bbtvpro3  GGGCCGAAGG CCCGTGAGCA ATATGCGTCG AAATA..AT.. ..........
bbtvpro4  GGGCCGAAGG CCCGTGAGCA ATATGCGTCG AAATA..AT.. ..........
bbtvpro6  GGGCCGCAGG CCCGTTAAAA ATAATAATCG AATTATAA.. ..........
bbtvpro2  GGGCCGCAGG CCCGTCAAGT TGAATGAACG GTCCAGATTA ATTCCTTAGC 301                                                    350
bbtvpro1  GACAAAAGCA CACTATGACA AAAGTACGGG TATCTGATTG GGTTATCTTA
bbtvpro5  AATACAA.CA CACTATAACA AATGTACGGG TATTTGATTG GGCTATATTA
bbtvpro3  GTTAACAAA  CAAATATACA TGATACGGAT AGTTGAATAC ATAAACAACG
bbtvpro4  GTTAACAAA  CAAATATACA TGATACGGAT AGTTGAATAC ATAAACAACG
bbtvpro6  ACGTTAGATA ATAATCAGAG ATAGGTGATC AGATAATATA AACATAAACG
bbtvpro2  GACGAAGAAA GGAATCTTAA AGGGACCAC  ATTAAAGACA GCTGTCATTG 351                                                    400
bbtvpro1  A.CGATCTAG GGCCGTAGGC CCG....... .......... ..........
bbtvpro5  ACCCCTTAAG GGCCGAAGGC CCGTTTAAAT ATGTGTTGGA CGAAGTCCAA
bbtvpro3  AGGTATACAA TACAACAAAC TGTTGTAAAG AAATA..AAA AATAAGAAGA
bbtvpro4  AGGTATACAA TACAACAAAC TGTTGTAAAG AAATA..AAA AATAAGAAGA
bbtvpro6  AAGTATATGC CGGTACAATA ATAAAATAAG TAATAACAAA AAAAATATGT
bbtvpro2  ATTAAATAAA TAATATAATA ACCAAAAGAC CTTTGTACCC TTCCTAATGA 401                                                    450
bbtvpro1  .......... .......... .......... ..TGAGCAAT GAAC......
bbtvpro5  ACACAAAAAA GTAAGCAGAA CAA.CGGAAT AATATGAGCT GGCA......
bbtvpro3  GAGAGTATAT TTGTGTCGGA TAAGCATCAC ACCCACCACT TTAG......
bbtvpro4  GATAGTATAT TTGTGTTGGA TAAGCCTTGC AACCACCACT TTAG......
bbtvpro6  ATACTAATCT CTGATTGGTT CAGGAGAAAG GCCCACCAAC TAAA......
bbtvpro2  TGACGTATAG GGGTGTCCCG ATGTAATTTA ACATAGCTCT GAAAAGAGAT 451                                                    500
bbtvpro1  .........G GCGAGATCAG ATGTCCCGAG TTAGTGCG.. ..........
bbtvpro5  .........A CGTAGGGTCC ATGTCCCGAG TTAGTGCG.. ..........
bbtvpro3  .........T GGTGGGCCAG ATGTCCCGAG TTAGTGCG.. ..........
bbtvpro4  .........T GGTGGGCCAG ATGTCCCGAG TTAGTGCG.. ..........
bbtvpro6  .........A GGTGGGAGA  ATGTCCCGA. .......... ..........
bbtvpro2  ATGGGCCGTT GGATGCCTCC ATCGGACGAT GGAGGTTGAA TGAACTTCTG
```

FIG. 11B

```
           501                                                        550
bbtvpro1   .CCACGTAAG CGCTGGGGCT TATTATTACC CCCAGCGCTC GGGACGGGAC
bbtvpro5   .CCACGTAAG CGCTGGGGCT TATTATTACC CCCAGCGCTC GGGACGGGAC
bbtvpro3   .CCACGTAAG CGCTGGGGAC TATTATTACC CCCAGCGCTC GGGACGGGAC
bbtvpro4   .CCACGTAAG CGCTGGGGCT TATTATTACC CCCAGCGCTC GGGACGGGAC
bbtvpro6   .TGACGTAAG CACGGGGAC  TATTATTACC CCCCGTGCTC GGGACGGGAC
bbtvpro2   CTGACGTAGG CGCTGGGGCT TATTATTACC CCCAGCGC.C GGGACGGGAC 551                                                        600
bbtvpro1   ATTTGCATCT ATAAATAGAC .......... .CTCCCCCCT CTCCATTACA
bbtvpro5   ATCACGTGCA ACTAACAGAC GCACGTGAGA ATGCAGTAGC TTGCAGCGAA
bbtvpro3   ATGGGCTAAT GGA....... ....TTGTGG ATATAGGGCC CAAAGGGCCC
bbtvpro4   ATCACGTGCG TCAACAAATG CACGTGACTG ATATAAGGGA CATAACGGGT
bbtvpro6   ATGACGTCAG CAAGGATTAT AATGGGCTTT TTATTAGCCC ATTTATTGAA
bbtvpro2   ATGGGCTTTT TAAATGGGCT TTGCGAGTTT GAACAGTTCA GTATCTTCGT 601                                                        650
bbtvpro1   AGATCATCAT CGACGACAGA .......... .......... ..........
bbtvpro5   AGATAGACGT CAACATCAAT AAAGAAGAAG GAATATTCTT TGCTTCGGCA
bbtvpro3   GTTAGATGG  GTTTGGGCT  CATGGCTTT  ATCCAGAAGA CCAAAAACAG
bbtvpro4   TTAGATAACG GTTTATGCGG ATTAGAATAT AACGTCACGT GTGAAAGCCG
bbtvpro6   TT..GGGCCG GGTTTTGTCA TTTTACAAAA GCCCGGTCCA GGATAAGTAT
bbtvpro2   TATTGGGCCA ACCCGGCCCA ATAATTAAGA GAACGTGTTC AAATTCGTGG 651                                                        700
bbtvpro1   .......... .......... .......... .......... ..........
bbtvpro5   CGAAGCAAAG GGTATAGATA TTTGTTCGAG ATGCGAAAAT GGAGGCTATT
bbtvpro3   GCGGGAACCG TCCCAA.... .......... ......ATTC AAACTTCGAT
bbtvpro4   AAAGGCACGT GACGAAGACA AATGGATTGA ATAAACATTT GACGTCCGGT
bbtvpro6   AATGTCACGT GCCGAATTAA AAGGTTGCTT CGCCACGAAG AAACCTAATT
bbtvpro2   TATGACCGAA GGTCAAGGTA ACCGGTCAAC ATTATTCTGG CTTGCGCAGC 701                                                        750
bbtvpro1   .......... .......... .......... .......... ..........
bbtvpro5   TAAACCTGAT GGTTTTGTGA TTTCCGAAAT CACTCGTCGG AAGAGAA...
bbtvpro3   ..TGCTTGCC CTGCAACGCA TCTAGAAGTC TATAAATACC AGTGTCTAGA
bbtvpro4   ..AGCTTCCG AAGGAAGTAA GCTTCGCGGC GAAGCAAACC ATTTATATAT
bbtvpro6   TGAGGTTGCG TATTCAATAC GCTACCGAAT ATCTATTAAT ATGTGAGTCT
bbtvpro2   AAGATACACG AATTAATTTA TTAATTCGTA GGACACGTGG ACGGACCGAA 751                                                        800
bbtvpro1   .......... .......... .......... .......... ..........
bbtvpro5   .......... .......... .......... .......... ..........
bbtvpro3   TAG....... .......... .......... .......... ..........
bbtvpro4   TTGCGTAGGC TTGCGGCCTA TAAATAGGAC GCAGCTAA.. ..........
bbtvpro6   CTGCCGAAAA AAATCAGAGC GAAAGCGGAA GGCAGAAGCG ..........
bbtvpro2   ATACTCTTGC ATCTCTATAA ATACCCTAAT CCTGTCAAGG ATAATTGCTC
```

FIG. 11C

```
         801                                                    850
bbtvpro1  .......... .......... .......... .......... ..........
bbtvpro5  .......... .......... .......... .......... ..........
bbtvpro3  .......... .......... .......... .......... ..........
bbtvpro4  .......... .......... .......... .......... ..........
bbtvpro6  .......... .......... .......... .......... ..........
bbtvpro2  TCTCTCTTCT GTCAAGGTGG TTGTGCTGAG GGGAAGATC  GCCAGCGGCG 851        871
bbtvpro1  .......... .......... .
bbtvpro5  .......... .......... .
bbtvpro3  .......... .......... .
bbtvpro4  .......... .......... .
bbtvpro6  .......... .......... .
bbtvpro2  ATCGTCGGAA CGACCTGCAT A
```

FIG. 11D

```
ATAAAACGAAGGCGATGAATAGCTGGAGAACTTCTTTCAGTGCTTGGACATCAGAGGTGG
AGAATATCATGGCGCAGCCATGTCATCGGAGAATAATTTGGGTCTATGGCCCAAATGGAG
GAGAAGGAAAGACAACGTATGCAAAACATCTAATGAAGACGAGAAATGCGTTTTATTCTC
CAGGAGGAAAATCATTGGATATATGTAGACTGTATAATTACGAGGATATTGTTATATTTG
ATATTCCAAGATGCAAAGAGGATTATTTAAATTATGGGTTATTAGAGGAATTTAAGAATG
GAATAATTCAAAGCGGGAAATATGAACCCGTTTTGAAGATAGTAGAATATGTCGAAGTCA
TTGTAATGGCTAACTTCCTTCCGAAGGAAGGAATCTTTTCTGAAGATCGAATAAAGTTGG
TTTCTTGCTGAACAAGTAATGACTTTACAGCGCACGCTCCGACAAAAGCACACTATGACA
AAAGTACGGGTATCTGATTGGGTTATCTTAACGATCTAGGGCCGTAGGCCCGTGAGCAAT
GAACGGCGAGATCAGATGTCCCGAGTTAGTGCGCCACGTAAGCGCTGGGGCTTATTATTA
CCCCCAGCGCTCGGGACGGGACATTTGCATCTATAAATAGACCTCCCCCCTCTCCATTAC
AAGATCATCATCGACGACAGAATGGCGCGATATGTGGTATGCTGGATGTTCACCATCAAC
AATCCCACAACACTACCAGTGATGAGGGATGAGATAAAATATATGGTATATCAAGTGGAG
AGGGGACAGGAGGGTACTCGTCATGTGCAAGGTTATGTCGAGATGAAGAGACGAAGCTCT
CTGAAGCAGATGAGAGGCTTCTTCCCAGGCGCACACCTTGAGAAACGAAAGGGAAGCCAA
GAAGAAGCGCGGTCATACTGTATGAAGGAAGATACAAGAATCGAAGGTCCCTTCGAGTTT
GGTTCATTTAAATTGTCATGTA
```

FIG. 12

```
AGTTGTGCTGTAATGTTAATTAATAAAACGTATATTTGGGAAATTGATAGTTGTATAAAACATACAACACACTAT
GAAATACAAGACGCTATGACAAATGTACGGGTATCTGAATGAGTTTTAGTATCGCTTAAGGGCCGCAGGCCCGTT
AAAAATAATAATCGAATTATAAACGTTAGATAATAATCAGAGATAGGTGATCAGATAATATAAACATAAACGAAG
TATATGCCGGTACAATAATAAAATAAGTAATAACAAAAAAAATATGTATACTAATCTCTGATTGGTTCAGGAGAA
AGGCCCACCAACTAAAAGGTGGGGAGAATGTCCCGATGACGTAAGCACGGGGGACTATTATTACCCCCCGTGCTC
GGGACGGGACATGACGTCAGCAAGGATTATAATGGGCTTTTTATTAGCCCATTTATTGAATTGGGCCGGGTTTTG
TCATTTTACAAAAGCCCGGTCCAGGATAAGTATAATGTCACGTGCCGAATTAAAAGGTTGCTTCGCCACGAAGAA
ACCTAATTTGAGGTTGCGTATTCAATACGCTACCGAATATCTATTAATATGTGAGTCT
CTGCCGAAAAAAATCAGAGCGAAAGCGGAAGGCAGAAGC
```

FIG. 13A

```
GTATACTAATCTCTGATTGGTTCAGGAGAAAGGCCCACCAACTAAAAGGTGGGGAGAATGTCCCGATGACGTA AG
CACGGGGGACTATTATTACCCCCCGTGCTCGGGACGGGACATGACGTCAGCAAGGATTATAATGGGCTTTTTATT
AGCCCATTTATTGAATTGGGCCGGGTTTTGTCATTTTACAAAAGCCCGGTCCAGGATAAGTATAATGTCACGTGC
CGAATTAAAAGGTTGCTTCGCCACGAAGAAACCTAATTTGAGGTTGCGTATTCAATACGCTACCGAATATCTATT
AATATGTGAGTCTCTGCCGAAAAAAATCAGAGCGAAAGCGGAAGGCAGAAGC
```

FIG. 13B

```
CATGACGTCAGCAAGGATTATAATGGGCTTTTTATTAGCCCATTTATTGAATTGGGCCGGGTTTTGTCATTTTAC
AAAAGCCCGGTCCAGGATAAGTATAATGTCACGTGCCGAATTAAAAGGTTGCTTCGCCACGAAGAAACCTAATTT
GAGGTTGCGTATTCAATACGCTACCGAATATCTATTAATATGTGAGTCTCTGCCGAAAAAAATCAGAGCGAAAGC
GGAAGGCAGAAGC
```

FIG. 13C

```
CCGGGTTTTGTCATTTTACAAAAGCCCGGTCCAGGATAAGTATAATGTCACGTGCCGAATTAAAAGGTTGCTTCG
CCACGAAGAAACCTAATTTGAGGTTGCGTATTCAATACGCTACCGAATATCTATTAATATGTGAGTCTCTGCCGA
AAAAAATCAGAGCGAAAGCGGAAGGCAGAAGC
```

FIG. 13D 6,127,604

SEQUENCE LISTING

<160> NUMBER OF SEQ ID NOS: 61

<210> SEQ ID NO 1
<211> LENGTH: 1060
<212> TYPE: DNA
<213> ORGANISM: Banana Bunchy Top Virus (BBTV)

<400> SEQUENCE: 1

```
ggcgctgggg cttattatta cccccagcgc cgggacggga catgggcttt ttaaatgggc      60
tttgcgagtt tgaacagttc agtatcttcg ttattgggcc aacccggccc aataattaag     120
agaacgtgtt caaattcgtg gtatgaccga aggtcaaggt aaccggtcaa cattattctg     180
gcttgcgcag caagatacac gaattaattt attaattcgt aggacacgtg gacggaccga     240
aatactcttg catctctata aataccctaa tcctgtcaag gataattgct ctctctcttc     300
tgtcaaggtg gttgtgctga ggcggaagat cgccagcggc gatcgtcgga acgacctgca     360
tctagagagg cggcgaggaa actacgaagc gtatatcggg tatttataga cttatagcgt     420
agctagaagt atacactgta cagatattgt atcttgtaaa ttacgaagca attcgtattt     480
gatattaata aaacaactgg gtttgttaat gtttacatta actagtatct tatatgtaca     540
aattaaaata cagtatacgg aacgtatact aacgtaaaaa ttaaatgata ggcgaagcat     600
gattaacagg tgtttaggta taattaacat aattatgaga agtaataata atacggaaaa     660
tgaataagta tgaggtgaaa gaggagatat tagaatattt aaaaacccaa ttatattatt     720
ttggaacgaa atacaacacg ctatgaaata caagacgcta tgacaaatgt acgggaatat     780
gattgtgtat cttaacgtat aagggccgca ggcccgtcaa gttgaatgaa cggtccagat     840
taattcctta gcgacgaaga aaggaatctt aaagggacc acattaaaga cagctgtcat     900
tgattaaata aataatataa taaccaaaag acctttgtac ccttcctaat gatgacgtat     960
aggggtgtcc cgatgtaatt taacatagct ctgaaaagag atatgggccg ttggatgcct    1020
ccatcggacg atggaggttg aatgaacttc tgctgacgta                          1060
```

<210> SEQ ID NO 2
<211> LENGTH: 1075
<212> TYPE: DNA
<213> ORGANISM: Banana Bunchy Top Virus (BBTV)
<220> FEATURE:
<221> NAME/KEY: CDS
<222> LOCATION: (213)...(737)

-continued

```
<400> SEQUENCE: 2
agcgctgggg actattatta cccccagcgc tcgggacggg acatgggcta atggattgtg     60
gatatagggc ccaaagggcc cgtttagatg ggttttgggc tcatgggctt tatccagaag    120
accaaaaaca ggcgggaacc gtcccaaatt caaacttcga ttgcttgccc tgcaacgcat    180
ctagaagtct ataaatacca gtgtctagat ag atg ttc aga caa gaa atg gct    233
                                    Met Phe Arg Gln Glu Met Ala
                                     1               5 agg tat ccg aag aaa tcc atc aag aag agg cgg gtt ggg cgc cgg aag    281
Arg Tyr Pro Lys Lys Ser Ile Lys Lys Arg Arg Val Gly Arg Arg Lys
         10                  15                  20 tat ggc agc aag gcg gca acg agc cac gac tac tcg tcg tca ggg tca    329
Tyr Gly Ser Lys Ala Ala Thr Ser His Asp Tyr Ser Ser Ser Gly Ser
     25                  30                  35 ata ttg gtt cct gaa aac acc gtc aag gta ttt cgg att gag cct act    377
Ile Leu Val Pro Glu Asn Thr Val Lys Val Phe Arg Ile Glu Pro Thr
 40                  45                  50                  55 gat aaa aca tta ccc aga tat ttt atc tgg aaa atg ttt atg ctt ctt    425
Asp Lys Thr Leu Pro Arg Tyr Phe Ile Trp Lys Met Phe Met Leu Leu
                 60                  65                  70 gtg tgc aag gtg aag ccc gga aga ata ctt cat tgg gct atg atc aag    473
Val Cys Lys Val Lys Pro Gly Arg Ile Leu His Trp Ala Met Ile Lys
             75                  80                  85 agt tct tgg gaa atc aac cag ccg aca acc tgt ctg gaa gcc cca ggt    521
Ser Ser Trp Glu Ile Asn Gln Pro Thr Thr Cys Leu Glu Ala Pro Gly
         90                  95                 100 tta ttt att aaa cct gaa cac agc cat ctg gtt aaa ctg gta tgt agt    569
Leu Phe Ile Lys Pro Glu His Ser His Leu Val Lys Leu Val Cys Ser
    105                 110                 115 ggg gaa ctt gaa gca gga gtc gca aca gga aca tca gat gtt gaa tgt    617
Gly Glu Leu Glu Ala Gly Val Ala Thr Gly Thr Ser Asp Val Glu Cys
120                 125                 130                 135 ctt ttg agg aag aca acc gtg ttg agg aag aat gta aca gag gtg gat    665
Leu Leu Arg Lys Thr Thr Val Leu Arg Lys Asn Val Thr Glu Val Asp
                140                 145                 150 tat tta tat ttg gca ttc tat tgt agt tct gga gta agt ata aac tac    713
Tyr Leu Tyr Leu Ala Phe Tyr Cys Ser Ser Gly Val Ser Ile Asn Tyr
            155                 160                 165 cag aac aga att aca tat cat gtt tgatatgttt atgtaaacat aaactattgt   767
Gln Asn Arg Ile Thr Tyr His Val
        170                 175 atggaatgaa atccaaataa catacaacac gctatgaaat acaagacgct atgacaaaag    827
tactggtata tgattaggta tcctaacgat ctagggccga aggcccgtga gcaatatgcg    887
tcgaaataat gtttaacaaa caaatataca tgatacggat agttgaatac ataaacaacg    947
aggtatacaa tacaacaaac tgttgtaaag aaataaaaaa taagaagaga gagtatattt   1007
gtgtcggata agcatcacac ccaccacttt agtggtgggc cagatgtccc gagttagtgc   1067
gccacgta                                                            1075

<210> SEQ ID NO 3
<211> LENGTH: 175
<212> TYPE: PRT
<213> ORGANISM: Banana Bunchy Top Virus (BBTV)

<400> SEQUENCE: 3

Met Phe Arg Gln Glu Met Ala Arg Tyr Pro Lys Lys Ser Ile Lys Lys
 1               5                  10                  15

-continued

```
Arg Arg Val Gly Arg Arg Lys Tyr Gly Ser Lys Ala Ala Thr Ser His
            20                  25                  30

Asp Tyr Ser Ser Ser Gly Ser Ile Leu Val Pro Glu Asn Thr Val Lys
        35                  40                  45

Val Phe Arg Ile Glu Pro Thr Asp Lys Thr Leu Pro Arg Tyr Phe Ile
    50                  55                  60

Trp Lys Met Phe Met Leu Leu Val Cys Lys Val Lys Pro Gly Arg Ile
 65                  70                  75                  80

Leu His Trp Ala Met Ile Lys Ser Ser Trp Glu Ile Asn Gln Pro Thr
                85                  90                  95

Thr Cys Leu Glu Ala Pro Gly Leu Phe Ile Lys Pro Glu His Ser His
            100                 105                 110

Leu Val Lys Leu Val Cys Ser Gly Glu Leu Glu Ala Gly Val Ala Thr
        115                 120                 125

Gly Thr Ser Asp Val Glu Cys Leu Leu Arg Lys Thr Thr Val Leu Arg
    130                 135                 140

Lys Asn Val Thr Glu Val Asp Tyr Leu Tyr Leu Ala Phe Tyr Cys Ser
145                 150                 155                 160

Ser Gly Val Ser Ile Asn Tyr Gln Asn Arg Ile Thr Tyr His Val
                165                 170                 175

<210> SEQ ID NO 4
<211> LENGTH: 1043
<212> TYPE: DNA
<213> ORGANISM: Banana Bunchy Top Virus (BBTV)
<220> FEATURE:
<221> NAME/KEY: CDS
<222> LOCATION: (279)...(629)

<400> SEQUENCE: 4
agcgctgggg cttattatta cccccagcgc tcgggacggg acatcacgtg cgtcaacaaa      60
tgcacgtgac tgatataagg gacataacgg gtttagataa cggtttatgc ggattagaat     120
ataacgtcac gtgtgaaagc cgaaaggcac gtgacgaaga caaatggatt gaataaacat     180
ttgacgtccg gtagcttccg aaggaagtaa gcttcgcggc gaagcaaacc atttatatat     240
ttgcgtaggc ttgcggccta taaataggac gcagctaa atg gca tta aca aca gag     296
                                          Met Ala Leu Thr Thr Glu
                                            1               5 cgg gtg aaa cta ttc ttt gaa tgg ttt ctg ttc ttt gga gca ata ttt       344
Arg Val Lys Leu Phe Phe Glu Trp Phe Leu Phe Phe Gly Ala Ile Phe
            10                  15                  20 att gcg att aca ata tta tat ata ttg ttg gtt ttg ctc ttt gag gta       392
Ile Ala Ile Thr Ile Leu Tyr Ile Leu Leu Val Leu Leu Phe Glu Val
        25                  30                  35 ccc agg tat att aag gag ctc gtg agg tgt ttg gta gaa tac ctg acc       440
Pro Arg Tyr Ile Lys Glu Leu Val Arg Cys Leu Val Glu Tyr Leu Thr
    40                  45                  50 aga cga cgt gta tgg atg cag agg acg cag ttg acg gag gca act gga       488
Arg Arg Arg Val Trp Met Gln Arg Thr Gln Leu Thr Glu Ala Thr Gly
 55                  60                  65                  70 gat gta gag atc ggc aga ggt att gtg gaa gac aga cga gat caa gaa       536
Asp Val Glu Ile Gly Arg Gly Ile Val Glu Asp Arg Arg Asp Gln Glu
                75                  80                  85

```
ccg gct gtc ata cca cat gta tct cag gta atc cct tct caa cca aat    584
Pro Ala Val Ile Pro His Val Ser Gln Val Ile Pro Ser Gln Pro Asn
             90                  95                 100 aga agg gat gat caa gga aga cga gga aac gct gga cct atg ttc        629
Arg Arg Asp Asp Gln Gly Arg Arg Gly Asn Ala Gly Pro Met Phe
        105                 110                 115 taatacacgg tatattaata tacgaaatat aaatgggtat tgatgtaaat gatcatacat  689
aatatatgta tgataatgaa acatattgta atatgtgaat tgtaaacgag agttgtatgt  749
ataaaacata caacacgcta tgaaatacaa gacgctatga caaaagtact ggtatatgat  809
taggtatcct aacgatctag ggccgaaggc ccgtgagcaa tatgcgtcga aataatgttt  869
aacaaacaaa tatacatgat acggatagtt gaatacataa caacgaggt atacaataca  929 acaaactgtt gtaaagaaat aaaaaataag aagagatagt atatttgtgt tggataagcc  989
ttgcaaccac cactttagtg gtgggccaga tgtcccgagt tagtgcgcca cgta        1043

<210> SEQ ID NO 5
<211> LENGTH: 117
<212> TYPE: PRT
<213> ORGANISM: Banana Bunchy Top Virus (BBTV)

<400> SEQUENCE: 5

Met Ala Leu Thr Thr Glu Arg Val Lys Leu Phe Phe Glu Trp Phe Leu
 1               5                  10                  15

Phe Phe Gly Ala Ile Phe Ile Ala Ile Thr Ile Leu Tyr Ile Leu Leu
            20                  25                  30

Val Leu Leu Phe Glu Val Pro Arg Tyr Ile Lys Glu Leu Val Arg Cys
         35                  40                  45

Leu Val Glu Tyr Leu Thr Arg Arg Val Trp Met Gln Arg Thr Gln
     50                  55                  60

Leu Thr Glu Ala Thr Gly Asp Val Glu Ile Arg Gly Ile Val Glu
 65                  70                  75                  80

Asp Arg Arg Asp Gln Glu Pro Ala Val Ile Pro His Val Ser Gln Val
                85                  90                  95

Ile Pro Ser Gln Pro Asn Arg Arg Asp Asp Gln Gly Arg Arg Gly Asn
            100                 105                 110

Ala Gly Pro Met Phe
        115

<210> SEQ ID NO 6
<211> LENGTH: 1018
<212> TYPE: DNA
<213> ORGANISM: Banana Bunchy Top Virus (BBTV)
<220> FEATURE:
<221> NAME/KEY: CDS
<222> LOCATION: (240)...(722)

<400> SEQUENCE: 6
agcgctgggg cttattatta cccccagcgc tcgggacggg acatcacgtg caactaacag   60
acgcacgtga gaatgcagta gcttgcagcg aaagatagac gtcaacatca ataaagaaga  120
aggaatattc tttgcttcgg cacgaagcaa agggtataga tatttgttcg agatgcgaaa  180
atggaggcta tttaaacctg atggttttgt gatttccgaa atcactcgtc ggaagagaa   239 atg gag ttc tgg gaa tcg tct gcc atg cct gac gat gtc aag aga gag   287
Met Glu Phe Trp Glu Ser Ser Ala Met Pro Asp Asp Val Lys Arg Glu
 1               5                  10                  15
```

```
att aag gaa ata tat tgg gaa gat cgg aag aaa ctt ctg ttc tgt cag      335
Ile Lys Glu Ile Tyr Trp Glu Asp Arg Lys Lys Leu Leu Phe Cys Gln
             20                  25                  30 aag ttg aag agc tat gtc aga agg att ctt gtt tat gga gat caa gag      383
Lys Leu Lys Ser Tyr Val Arg Arg Ile Leu Val Tyr Gly Asp Gln Glu
         35                  40                  45 gat gcc ctt gcc gga gtg aag gat atg aag act tct att att cgc tat      431
Asp Ala Leu Ala Gly Val Lys Asp Met Lys Thr Ser Ile Ile Arg Tyr
 50                  55                  60 agc gaa tac ttg aag aaa cca tgt gtg gta att tgt tgt gtt agc aat      479
Ser Glu Tyr Leu Lys Lys Pro Cys Val Val Ile Cys Cys Val Ser Asn
 65                  70                  75                  80 aaa tca att gtg tat agg tta aac agc atg gtg ttc ttt tat cat gaa      527
Lys Ser Ile Val Tyr Arg Leu Asn Ser Met Val Phe Phe Tyr His Glu
             85                  90                  95 tac ctt gaa gaa cta ggt ggt gat tac tca gta tat caa gat ctc tat      575
Tyr Leu Glu Glu Leu Gly Gly Asp Tyr Ser Val Tyr Gln Asp Leu Tyr
            100                 105                 110 tgt gat gag gta ctc tct tct tca tcg aca gag gaa gaa gat gta gga      623
Cys Asp Glu Val Leu Ser Ser Ser Ser Thr Glu Glu Glu Asp Val Gly
        115                 120                 125 gta ata tat agg aat gtt atc atg gca tcg aca caa gag aag ttc tct      671
Val Ile Tyr Arg Asn Val Ile Met Ala Ser Thr Gln Glu Lys Phe Ser
    130                 135                 140 tgg agt gat tgt cag cag ata gtt ata tca gac tat gat gta aca tta      719
Trp Ser Asp Cys Gln Gln Ile Val Ile Ser Asp Tyr Asp Val Thr Leu
145                 150                 155                 160 ctc taatgtaata tccattatca tcaataaaat aatggaatgt tgattatgta           772
Leu tttatcataa atacataatg gtacgtat agcataaaat acattaacca acatacaaca      832
cactataaaa tacaacacgc tatgacaaat gtacgggtat atgattgggt tatattaacc    892
ccttaagggc cgaaggcccg tttaaatatg tgttggacga agtccaaaca caaaaaagta    952
agcagaacaa cggaataata tgagctggca acgtagggtc catgtcccga gttagtgcgc   1012
cacgta                                                              1018

<210> SEQ ID NO 7
<211> LENGTH: 161
<212> TYPE: PRT
<213> ORGANISM: Banana Bunchy Top Virus (BBTV)

<400> SEQUENCE: 7

Met Glu Phe Trp Glu Ser Ser Ala Met Pro Asp Asp Val Lys Arg Glu
 1               5                  10                  15

Ile Lys Glu Ile Tyr Trp Glu Asp Arg Lys Lys Leu Leu Phe Cys Gln
             20                  25                  30

Lys Leu Lys Ser Tyr Val Arg Arg Ile Leu Val Tyr Gly Asp Gln Glu
         35                  40                  45

Asp Ala Leu Ala Gly Val Lys Asp Met Lys Thr Ser Ile Ile Arg Tyr
 50                  55                  60

Ser Glu Tyr Leu Lys Lys Pro Cys Val Val Ile Cys Cys Val Ser Asn
 65                  70                  75                  80

Lys Ser Ile Val Tyr Arg Leu Asn Ser Met Val Phe Phe Tyr His Glu
             85                  90                  95

Tyr Leu Glu Glu Leu Gly Gly Asp Tyr Ser Val Tyr Gln Asp Leu Tyr
            100                 105                 110

Cys Asp Glu Val Leu Ser Ser Ser Ser Thr Glu Glu Glu Asp Val Gly
        115                 120                 125
```

```
Val Ile Tyr Arg Asn Val Ile Met Ala Ser Thr Gln Glu Lys Phe Ser
        130                 135                 140

Trp Ser Asp Cys Gln Gln Ile Val Ile Ser Asp Tyr Asp Val Thr Leu
145                 150                 155                 160

Leu

<210> SEQ ID NO 8
<211> LENGTH: 1089
<212> TYPE: DNA
<213> ORGANISM: Banana Bunchy Top Virus (BBTV)
<220> FEATURE:
<221> NAME/KEY: CDS
<222> LOCATION: (281)...(742)

<400> SEQUENCE: 8
agcacggggg actattatta cccccgtgc tcgggacggg acatgacgtc agcaaggatt     60
ataatgggct ttttattagc ccatttattg aattgggccg ggttttgtca ttttacaaaa    120
gcccggtcca ggataagtat aatgtcacgt gccgaattaa aaggttgctt cgccacgaag    180
aaacctaatt tgaggttgcg tattcaatac gctaccgaat atctattaat atgtgagtct    240
ctgccgaaaa aaatcagagc gaaagcggaa ggcagaagcg atg gat tgg gcg gaa      295
                                              Met Asp Trp Ala Glu
                                                1               5 tca caa ttc aag acc tgt act cat gga tgc gat tgg aag aag ata tca     343
Ser Gln Phe Lys Thr Cys Thr His Gly Cys Asp Trp Lys Lys Ile Ser
          10                  15                  20 tcg gat tca gcc gat aat cga caa tat gta cca tgc gtc gat tct gga     391
Ser Asp Ser Ala Asp Asn Arg Gln Tyr Val Pro Cys Val Asp Ser Gly
              25                  30                  35 gct gga aga aag tcg cct cgc aag gta ctt ctt aga tct att gaa gct     439
Ala Gly Arg Lys Ser Pro Arg Lys Val Leu Leu Arg Ser Ile Glu Ala
         40                  45                  50 gtg ttt aac gga agc ttc agc gga aat aat agg aat gtt cgt gga ttt     487
Val Phe Asn Gly Ser Phe Ser Gly Asn Asn Arg Asn Val Arg Gly Phe
      55                  60                  65 ctc tac gta tcg atc aga gac gat gac gga gaa atg cgt cca gta ctc     535
Leu Tyr Val Ser Ile Arg Asp Asp Asp Gly Glu Met Arg Pro Val Leu
 70                  75                  80                  85 ata gta cca ttc gga gga tat gga tat cat aat gat ttt tat tat ttc     583
Ile Val Pro Phe Gly Gly Tyr Gly Tyr His Asn Asp Phe Tyr Tyr Phe
                 90                  95                 100 gaa ggg aag ggg aaa gtt gaa tgt gat ata tca tca gat tat gtt gcg     631
Glu Gly Lys Gly Lys Val Glu Cys Asp Ile Ser Ser Asp Tyr Val Ala
             105                 110                 115 cca gga ata gat tgg agc aga gac atg gaa gtt agt att agt aac agc     679
Pro Gly Ile Asp Trp Ser Arg Asp Met Glu Val Ser Ile Ser Asn Ser
         120                 125                 130 aac aac tgt aat gaa tta tgt gat ctg aag tgt tat gtt gtt tgt tcg     727
Asn Asn Cys Asn Glu Leu Cys Asp Leu Lys Cys Tyr Val Val Cys Ser
     135                 140                 145 tta aga atc aag gaa taaaagttgt gctgtaatgt taattaataa aacgtatatt     782
Leu Arg Ile Lys Glu
150 tgggaaattg atagttgtat aaaacataca acacactatg aaatacaaga cgctatgaca    842 aatgtacggg tatctgaatg agttttagta tcgcttaagg gccgcaggcc cgttaaaaat    902 aataatcgaa ttataaacgt tagataataa tcagagatag gtgatcagat aatataaaca    962 taaacgaagt atatgccggt acaataataa aataagtaat aacaaaaaaa atatgtatac   1022
```

-continued

```
taatctctga ttggttcagg agaaaggccc accaactaaa aggtggggag aatgtcccga    1082
tgacgta                                                              1089
```

<210> SEQ ID NO 9
<211> LENGTH: 154
<212> TYPE: PRT
<213> ORGANISM: Banana Bunchy Top Virus (BBTV)

<400> SEQUENCE: 9

```
Met Asp Trp Ala Glu Ser Gln Phe Lys Thr Cys Thr His Gly Cys Asp
 1               5                  10                  15

Trp Lys Lys Ile Ser Ser Asp Ser Ala Asp Asn Arg Gln Tyr Val Pro
            20                  25                  30

Cys Val Asp Ser Gly Ala Gly Arg Lys Ser Pro Arg Lys Val Leu Leu
        35                  40                  45

Arg Ser Ile Glu Ala Val Phe Asn Gly Ser Phe Ser Gly Asn Asn Arg
    50                  55                  60

Asn Val Arg Gly Phe Leu Tyr Val Ser Ile Arg Asp Asp Gly Glu
 65                 70                  75                  80

Met Arg Pro Val Leu Ile Val Pro Phe Gly Gly Tyr Gly Tyr His Asn
                85                  90                  95

Asp Phe Tyr Tyr Phe Glu Gly Lys Gly Lys Val Glu Cys Asp Ile Ser
            100                 105                 110

Ser Asp Tyr Val Ala Pro Gly Ile Asp Trp Ser Arg Asp Met Glu Val
        115                 120                 125

Ser Ile Ser Asn Ser Asn Asn Cys Asn Glu Leu Cys Asp Leu Lys Cys
    130                 135                 140

Tyr Val Val Cys Ser Leu Arg Ile Lys Glu
145                 150
```

<210> SEQ ID NO 10
<211> LENGTH: 69
<212> TYPE: DNA
<213> ORGANISM: Banana Bunchy Top Virus (BBTV)

<400> SEQUENCE: 10

```
atgtcccgag ttagtgcgcc acgtaagcgc tggggcttat tattacccc agcgctcggg    60 acgggacat                                                           69
```

<210> SEQ ID NO 11
<211> LENGTH: 53
<212> TYPE: DNA
<213> ORGANISM: Banana Bunchy Top Virus (BBTV)

<400> SEQUENCE: 11

```
tgctgacgta ggcgctgggg cttattatta ccccagcgc cgggacggga cat            53
```

<210> SEQ ID NO 12
<211> LENGTH: 69
<212> TYPE: DNA
<213> ORGANISM: Banana Bunchy Top Virus (BBTV)

<400> SEQUENCE: 12

```
atgtcccgag ttagtgcgcc acgtaagcgc tggggactat tattacccc agcgctcggg    60 acgggacat                                                           69
```

<210> SEQ ID NO 13
<211> LENGTH: 69

```
<212> TYPE: DNA
<213> ORGANISM: Banana Bunchy Top Virus (BBTV)

<400> SEQUENCE: 13
atgtcccgag ttagtgcgcc acgtaagcgc tggggcttat tattacccccc agcgctcggg     60 acgggacat                                                             69

<210> SEQ ID NO 14
<211> LENGTH: 69
<212> TYPE: DNA
<213> ORGANISM: Banana Bunchy Top Virus (BBTV)

<400> SEQUENCE: 14
atgtcccgag ttagtgcgcc acgtaagcgc tggggcttat tattacccccc agcgctcggg     60 acgggacat                                                             69

<210> SEQ ID NO 15
<211> LENGTH: 60
<212> TYPE: DNA
<213> ORGANISM: Banana Bunchy Top Virus (BBTV)

<400> SEQUENCE: 15
atgtcccgat gacgtaagca cgggggacta ttattacccc ccgtgctcgg gacgggacat     60

<210> SEQ ID NO 16
<211> LENGTH: 65
<212> TYPE: DNA
<213> ORGANISM: Banana Bunchy Top Virus (BBTV)

<400> SEQUENCE: 16
cacactatga caaaagtayg ggtatctgat tgggttatct aacgatcta gggccgtagg     60 cccgt                                                                 65

<210> SEQ ID NO 17
<211> LENGTH: 90
<212> TYPE: DNA
<213> ORGANISM: Banana Bunchy Top Virus (BBTV)

<400> SEQUENCE: 17
gaaatacaac acgctatgaa atacaagacg ctatgacaaa tgtaygggwa tmtgattgtg     60
tatcttaacg tataagggcc gcaggcccgt                                      90

<210> SEQ ID NO 18
<211> LENGTH: 90
<212> TYPE: DNA
<213> ORGANISM: Banana Bunchy Top Virus (BBTV)

<400> SEQUENCE: 18
aacatacaac acgctatgaa atacaagacg ctatgacaaa agtactggta tatgattagg     60
tatcctaacg atctagggcc gaaggcccgt                                      90

<210> SEQ ID NO 19
<211> LENGTH: 90
<212> TYPE: DNA
<213> ORGANISM: Banana Bunchy Top Virus (BBTV)

<400> SEQUENCE: 19
aacatacaac acgctatgaa atacaagacg ctatgacaaa agtactggta tatgattagg     60
tatcctaacg atctagggcc gaaggcccgt                                      90
```

-continued

```
<210> SEQ ID NO 20
<211> LENGTH: 92
<212> TYPE: DNA
<213> ORGANISM: Banana Bunchy Top Virus (BBTV)

<400> SEQUENCE: 20
aacatacaac acactataaa atacaacaca ctataacaaa tgtacgggta tttgattggg      60
ctatattaac cccttaaggg ccgaaggccc gt                                    92

<210> SEQ ID NO 21
<211> LENGTH: 91
<212> TYPE: DNA
<213> ORGANISM: Banana Bunchy Top Virus (BBTV)

<400> SEQUENCE: 21
aacatacaac acactatgaa atacaagacg ctatgacaaa tgtacgggta tctgaatgag      60
ttttagtatc gcttaagggc cgcaggcccg t                                     91

<210> SEQ ID NO 22
<211> LENGTH: 250
<212> TYPE: DNA
<213> ORGANISM: Banana Bunchy Top Virus (BBTV)

<400> SEQUENCE: 22
acaagtaatg actttacagc gcacgctccg acaaaagcac actatgacaa agtacgggt       60 atctgattgg gttatcttaa cgatctaggg ccgtaggccc gtgagcaatg aacggcgaga    120
tcagatgtcc cgagttagtg cgccacgtaa gcgctggggc ttattattac ccccagcgct    180
cgggacggga catttgcatc tataaataga cctccccccct ctccattaca agatcatcat    240
cgacgacaga                                                            250

<210> SEQ ID NO 23
<211> LENGTH: 869
<212> TYPE: DNA
<213> ORGANISM: Banana Bunchy Top Virus (BBTV)

<400> SEQUENCE: 23
tatacggaac gtatactaac gtaaaaatta aatgataggc gaagcatgat taacaggtgt      60
ttaggtataa ttaacataat tatgagaagt aataataata cggaaaatga ataagtatga    120
ggtgaaagag gagatattag aatatttaaa aacccaatta tattattttg gaacgaaata    180
caacacgcta tgaaatacaa gacgctatga caaatgtacg ggaatatgat tgtgtatctt    240
aacgtataag ggccgcaggc ccgtcaagtt gaatgaacgg tccagattaa ttccttagcg    300
acgaagaaag gaatcttaaa ggggaccaca ttaaagacag ctgtcattga ttaaataaat    360
aatataataa ccaaaagacc tttgtaccct tcctaatgat gacgtatagg ggtgtcccga    420
tgtaatttaa catagctctg aaaagagata tgggccgttg gatgcctcca tcggacgatg    480
gaggttgaat gaacttctgc tgacgtaggc gctgggcctt attattaccc ccagcgccgg    540
gacgggacat gggcttttta aatgggcttt gcgagtttga acgttcagt atcttcgtta     600 ttgggccaac ccggcccaat aattaagaga acgtgttcaa attcgtggta tgaccgaagg    660
tcaaggtaac cggtcaacat tattctggct tgcgcagcaa gatacacgaa ttaatttatt    720
aattcgtagg acacgtggac ggaccgaaat actcttgcat ctctataaat accctaatcc    780
tgtcaaggat aattgctctc tctcttctgt caaggtggtt gtgctgaggc ggaagatcgc    840
cagcggcgat cgtcggaacg acctgcata                                      869
```

<210> SEQ ID NO 24
<211> LENGTH: 547
<212> TYPE: DNA
<213> ORGANISM: Banana Bunchy Top Virus (BBTV)

<400> SEQUENCE: 24

| | | | | | |
|---|---|---|---|---|---|
| tatgtttatg | taaacataaa | ctattgtatg | gaatgaaatc | caaataacat | acaacacgct | 60 |
| atgaaataca | agacgctatg | acaaaagtac | tggtatatga | ttaggtatcc | taacgatcta | 120 |
| gggccgaagg | cccgtgagca | atatgcgtcg | aaataatgtt | taacaaacaa | atatacatga | 180 |
| tacggatagt | tgaatacata | aacaacgagg | tatacaatac | aacaaactgt | tgtaaagaaa | 240 |
| taaaaaataa | gaagagagag | tatatttgtg | tcggataagc | atcacaccca | ccactttagt | 300 |
| ggtgggccag | atgtcccgag | ttagtgcgcc | acgtaagcgc | tggggactat | tattaccccc | 360 |
| agcgctcggg | acgggacatg | ggctaatgga | ttgtggatat | agggcccaaa | gggcccgttt | 420 |
| agatgggttt | tgggctcatg | ggctttatcc | agaagaccaa | aaacaggcgg | gaaccgtccc | 480 |
| aaattcaaac | ttcgattgct | tgccctgcaa | cgcatctaga | agtctataaa | taccagtgtc | 540 |
| tagatag | | | | | | 547 |

<210> SEQ ID NO 25
<211> LENGTH: 689
<212> TYPE: DNA
<213> ORGANISM: Banana Bunchy Top Virus (BBTV)

<400> SEQUENCE: 25

| | | | | | |
|---|---|---|---|---|---|
| tacacggtat | attaatatac | gaaatataaa | tgggtattga | tgtaaatgat | catacataat | 60 |
| atatgtatga | taatgaaaca | tattgtaata | tgtgaattgt | aaacgagagt | tgtatgtata | 120 |
| aaacatacaa | cacgctatga | aatacaagac | gctatgacaa | agtactggt | atatgattag | 180 |
| gtatcctaac | gatctagggc | cgaaggcccg | tgagcaatat | gcgtcgaaat | aatgtttaac | 240 |
| aaacaaatat | acatgatacg | gatagttgaa | tacataaaca | acgaggtata | caatacaaca | 300 |
| aactgttgta | agaaataaa | aataagaag | agatagtata | tttgtgttgg | ataagccttg | 360 |
| caaccaccac | tttagtggtg | gccagatgt | cccgagttag | tgcgccacgt | aagcgctggg | 420 |
| gcttattatt | accccagcg | ctcgggacgg | gacatcacgt | gcgtcaacaa | atgcacgtga | 480 |
| ctgatataag | ggacataacg | ggtttagata | acggtttatg | cggattagaa | tataacgtca | 540 |
| cgtgtgaaag | ccgaaaggca | cgtgacgaag | acaaatggat | tgaataaaca | tttgacgtcc | 600 |
| ggtagcttcc | gaaggaagta | agcttcgcgg | cgaagcaaac | catttatata | tttgcgtagg | 660 |
| cttgcggcct | ataaatagga | cgcagctaa | | | | 689 |

<210> SEQ ID NO 26
<211> LENGTH: 532
<212> TYPE: DNA
<213> ORGANISM: Banana Bunchy Top Virus (BBTV)

<400> SEQUENCE: 26

| | | | | | |
|---|---|---|---|---|---|
| tgtaatatcc | attatcatca | ataaaataat | ggaatgttga | ttatgtattt | atcataaata | 60 |
| cataatggta | tacgtatagc | ataaaataca | ttaaccaaca | tacaacacac | tataaaatac | 120 |
| aacacactat | aacaaatgta | cgggtatttg | attgggctat | attaacccct | taagggccga | 180 |
| aggcccgttt | aaatatgtgt | tggacgaagt | ccaaacacaa | aaaagtaagc | agaacaacgg | 240 |
| aataaatgag | gctggcaacg | tagggtccat | gtcccgagtt | agtgcgccac | gtaagcgctg | 300 |
| gggcttatta | ttaccccag | cgctcgggac | gggacatcac | gtgcaactaa | cagacgcacg | 360 |

-continued

```
tgagaatgca gtagcttgca gcgaaagata gacgtcaaca tcaataaaga agaaggaata      420
ttctttgctt cggcacgaag caaagggtat agatatttgt tcgagatgcg aaaatggagg      480
ctatttaaac ctgatggttt tgtgatttcc gaaatcactc gtcggaagag aa              532
```

<210> SEQ ID NO 27
<211> LENGTH: 624
<212> TYPE: DNA
<213> ORGANISM: Banana Bunchy Top Virus (BBTV)

<400> SEQUENCE: 27

```
aagttgtgct gtaatgttaa ttaataaaac gtatatttgg gaaattgata gttgtataaa       60
acatacaaca cactatgaaa tacaagacgc tatgacaaat gtacgggtat ctgaatgagt      120
tttagtatcg cttaagggcc gcaggcccgt taaaaataat aatcgaatta taaacgttag      180
ataataatca gagataggtg atcagataat ataaacataa acgaagtata tgccggtaca      240
ataataaaat aagtaataac aaaaaaaata tgtatactaa tctctgattg gttcaggaga      300
aaggcccacc aactaaaagg tggggagaat gtcccgatga cgtaagcacg ggggactatt      360 attaccccccc gtgctcggga cgggacatga cgtcagcaag gattataatg gcttttttat      420
tagcccattt attgaattgg gccgggtttt gtcattttac aaaagcccgg tccaggataa      480
gtataatgtc acgtgccgaa ttaaaaggtt gcttcgccac gaagaaacct aatttgaggt      540
tgcgtattca atacgctacc gaatatctat taatatgtga gtctctgccg aaaaaaatca      600
gagcgaaagc ggaaggcaga agcg                                             624
```

<210> SEQ ID NO 28
<211> LENGTH: 982
<212> TYPE: DNA
<213> ORGANISM: Banana Bunchy Top Virus (BBTV)

<400> SEQUENCE: 28

```
ataaaacgaa ggcgatgaat agctggagaa cttctttcag tgcttggaca tcagaggtgg       60
agaatatcat ggcgcagcca tgtcatcgga gaataatttg ggtctatggc ccaaatggag      120
gagaaggaaa gacaacgtat gcaaaacatc taatgaagac gagaaatgcg ttttattctc      180
caggaggaaa atcattggat atatgtagac tgtataatta cgaggatatt gttatatttg      240
atattccaag atgcaaagag gattatttaa attatgggtt attagaggaa tttaagaatg      300
gaataattca aagcgggaaa tatgaacccg ttttgaagat agtagaatat gtcgaagtca      360
ttgtaatggc taacttcctt ccgaaggaag gaatcttttc tgaagatcga ataaagttgg      420
tttcttgctg aacaagtaat gactttacag cgcacgctcc gacaaaagca cactatgaca      480
aaagtacggg tatctgattg ggttatctta acgatctagg gccgtaggcc cgtgagcaat      540
gaacggcgag atcagatgtc ccgagttagt gcgccacgta agcgctgggg cttattatta      600
cccccagcgc tcgggacggg acatttgcat ctataaatag acctcccccc tctccattac      660
aagatcatca tcgacgacag aatggcgcga tatgtggtat gctggatgtt caccatcaac      720
aatcccacaa cactaccagt gatgagggat gagataaaat atatgtata tcaagtggag      780 aggggacagg agggtactcg tcatgtgcaa ggttatgtcg agatgaagag acgaagctct      840
ctgaagcaga tgagaggctt cttcccaggc gcacaccttg agaaacgaaa gggaagccaa      900
gaagaagcgc ggtcatactg tatgaaggaa gatacaagaa tcgaaggtcc cttcgagttt      960
ggttcattta aattgtcatg ta                                               982
```

-continued

<210> SEQ ID NO 29
<211> LENGTH: 622
<212> TYPE: DNA
<213> ORGANISM: Banana Bunchy Top Virus (BBTV)

<400> SEQUENCE: 29
agttgtgctg taatgttaat taataaaacg tatatttggg aaattgatag ttgtataaaa 60
catacaacac actatgaaat acaagacgct atgacaaatg tacgggtatc tgaatgagtt 120
ttagtatcgc ttaagggccg caggcccgtt aaaaataata atcgaattat aaacgttaga 180
taataatcag agataggtga tcagataata taaacataaa cgaagtatat gccggtacaa 240
taataaaata agtaataaca aaaaaaatat gtatactaat ctctgattgg ttcaggagaa 300
aggcccacca actaaaaggt ggggagaatg tcccgatgac gtaagcacgg gggactatta 360
ttaccccccg tgctcgggac gggacatgac gtcagcaagg attataatgg gctttttatt 420
agcccattta ttgaattggg ccgggttttg tcattttaca aaagcccggt ccaggataag 480
tataatgtca cgtgccgaat taaaaggttg cttcgccacg aagaaaccta atttgaggtt 540
gcgtattcaa tacgctaccg aatatctatt aatatgtgag tctctgccga aaaaaatcag 600
agcgaaagcg gaaggcagaa gc 622

<210> SEQ ID NO 30
<211> LENGTH: 352
<212> TYPE: DNA
<213> ORGANISM: Banana Bunchy Top Virus (BBTV)

<400> SEQUENCE: 30
gtatactaat ctctgattgg ttcaggagaa aggcccacca actaaaaggt ggggagaatg 60
tcccgatgac gtaagcacgg gggactatta ttaccccccg tgctcgggac gggacatgac 120
gtcagcaagg attataatgg gctttttatt agcccattta ttgaattggg ccgggttttg 180
tcattttaca aaagcccggt ccaggataag tataatgtca cgtgccgaat taaaaggttg 240
cttcgccacg aagaaaccta atttgaggtt gcgtattcaa tacgctaccg aatatctatt 300
aatatgtgag tctctgccga aaaaaatcag agcgaaagcg gaaggcagaa gc 352

<210> SEQ ID NO 31
<211> LENGTH: 238
<212> TYPE: DNA
<213> ORGANISM: Banana Bunchy Top Virus (BBTV)

<400> SEQUENCE: 31
catgacgtca gcaaggatta taatgggctt tttattagcc catttattga attgggccgg 60
gttttgtcat tttacaaaag cccggtccag gataagtata atgtcacgtg ccgaattaaa 120
aggttgcttc gccacgaaga aacctaattt gaggttgcgt attcaatacg ctaccgaata 180
tctattaata tgtgagtctc tgccgaaaaa aatcagagcg aaagcggaag gcagaagc 238

<210> SEQ ID NO 32
<211> LENGTH: 182
<212> TYPE: DNA
<213> ORGANISM: Banana Bunchy Top Virus (BBTV)

<400> SEQUENCE: 32
ccgggttttg tcattttaca aaagcccggt ccaggataag tataatgtca cgtgccgaat 60
taaaaggttg cttcgccacg aagaaaccta atttgaggtt gcgtattcaa tacgctaccg 120

```
aatatctatt aatatgtgag tctctgccga aaaaaatcag agcgaaagcg gaaggcagaa      180
gc                                                                     182

<210> SEQ ID NO 33
<211> LENGTH: 17
<212> TYPE: DNA
<213> ORGANISM: Banana Bunchy Top Virus (BBTV)

<400> SEQUENCE: 33
gcatccaacg gcccata                                                      17

<210> SEQ ID NO 34
<211> LENGTH: 17
<212> TYPE: DNA
<213> ORGANISM: Banana Bunchy Top Virus (BBTV)

<400> SEQUENCE: 34
ctccatcgga cgatgga                                                      17

<210> SEQ ID NO 35
<211> LENGTH: 17
<212> TYPE: DNA
<213> ORGANISM: Banana Bunchy Top Virus (BBTV)

<400> SEQUENCE: 35
tattagtaac agcaaca                                                      17

<210> SEQ ID NO 36
<211> LENGTH: 17
<212> TYPE: DNA
<213> ORGANISM: Banana Bunchy Top Virus (BBTV)

<400> SEQUENCE: 36
ctaacttcca tgtctct                                                      17

<210> SEQ ID NO 37
<211> LENGTH: 17
<212> TYPE: DNA
<213> ORGANISM: Banana Bunchy Top Virus (BBTV)

<400> SEQUENCE: 37
cgggwatmtg attgkgt                                                      17

<210> SEQ ID NO 38
<211> LENGTH: 17
<212> TYPE: DNA
<213> ORGANISM: Banana Bunchy Top Virus (BBTV)

<400> SEQUENCE: 38
tacwtttgtc atagygt                                                      17

<210> SEQ ID NO 39
<211> LENGTH: 30
<212> TYPE: DNA
<213> ORGANISM: Banana Bunchy Top Virus (BBTV)

<400> SEQUENCE: 39
ggtccccttt aagattcctt tcttcgtcgc                                        30

<210> SEQ ID NO 40
<211> LENGTH: 30
<212> TYPE: DNA
<213> ORGANISM: Banana Bunchy Top Virus (BBTV)
```

-continued

```
<400> SEQUENCE: 40
cggaaaatga ataagtatga ggtgaaagag                                          30

<210> SEQ ID NO 41
<211> LENGTH: 25
<212> TYPE: DNA
<213> ORGANISM: Banana Bunchy Top Virus (BBTV)

<400> SEQUENCE: 41
gcctgcagag ttgtgctgta atgtt                                               25

<210> SEQ ID NO 42
<211> LENGTH: 24
<212> TYPE: DNA
<213> ORGANISM: Banana Bunchy Top Virus (BBTV)

<400> SEQUENCE: 42
gcggatccgc ttctgccttc cgct                                                24

<210> SEQ ID NO 43
<211> LENGTH: 26
<212> TYPE: DNA
<213> ORGANISM: Banana Bunchy Top Virus (BBTV)

<400> SEQUENCE: 43
gccctgcagc atggacgtca gcaagg                                              26

<210> SEQ ID NO 44
<211> LENGTH: 24
<212> TYPE: DNA
<213> ORGANISM: Banana Bunchy Top Virus (BBTV)

<400> SEQUENCE: 44
gcctgcagac tattgtatgg aatg                                                24

<210> SEQ ID NO 45
<211> LENGTH: 23
<212> TYPE: DNA
<213> ORGANISM: Banana Bunchy Top Virus (BBTV)

<400> SEQUENCE: 45
gcggatccct atctagacac tgg                                                 23

<210> SEQ ID NO 46
<211> LENGTH: 23
<212> TYPE: DNA
<213> ORGANISM: Banana Bunchy Top Virus (BBTV)

<400> SEQUENCE: 46
gctctagaat gggtattgat gta                                                 23

<210> SEQ ID NO 47
<211> LENGTH: 25
<212> TYPE: DNA
<213> ORGANISM: Banana Bunchy Top Virus (BBTV)

<400> SEQUENCE: 47
gcggatcctt agctgcgtcc tattt                                               25

<210> SEQ ID NO 48
<211> LENGTH: 23
<212> TYPE: DNA
<213> ORGANISM: Banana Bunchy Top Virus (BBTV)
```

-continued

```
<400> SEQUENCE: 48
gcggatccga cgagtgattt cgg                                   23

<210> SEQ ID NO 49
<211> LENGTH: 17
<212> TYPE: DNA
<213> ORGANISM: Banana Bunchy Top Virus (BBTV)

<400> SEQUENCE: 49
gttatcatgg catcgac                                          17

<210> SEQ ID NO 50
<211> LENGTH: 17
<212> TYPE: DNA
<213> ORGANISM: Banana Bunchy Top Virus (BBTV)

<400> SEQUENCE: 50
gaacaagtaa tgactttt                                         17

<210> SEQ ID NO 51
<211> LENGTH: 30
<212> TYPE: DNA
<213> ORGANISM: Banana Bunchy Top Virus (BBTV)

<400> SEQUENCE: 51
ggaagaagcc tctcatctgc ttcagagagc                            30

<210> SEQ ID NO 52
<211> LENGTH: 28
<212> TYPE: DNA
<213> ORGANISM: Banana Bunchy Top Virus (BBTV)

<400> SEQUENCE: 52
ggatcctaca tgacaattta aatgaacc                              28

<210> SEQ ID NO 53
<211> LENGTH: 25
<212> TYPE: DNA
<213> ORGANISM: Banana Bunchy Top Virus (BBTV)

<400> SEQUENCE: 53
aagcttataa aacgaaggcg atgaa                                 25

<210> SEQ ID NO 54
<211> LENGTH: 16
<212> TYPE: DNA
<213> ORGANISM: Banana Bunchy Top Virus (BBTV)

<400> SEQUENCE: 54
atacaasacr ctatga                                           16

<210> SEQ ID NO 55
<211> LENGTH: 9
<212> TYPE: DNA
<213> ORGANISM: Banana Bunchy Top Virus (BBTV)

<400> SEQUENCE: 55 ctatwwawa                                                    9

<210> SEQ ID NO 56
<211> LENGTH: 8
<212> TYPE: DNA
<213> ORGANISM: Banana Bunchy Top Virus (BBTV)
```

-continued

<400> SEQUENCE: 56 tgacgtaa 8

<210> SEQ ID NO 57
<211> LENGTH: 6
<212> TYPE: DNA
<213> ORGANISM: Banana Bunchy Top Virus (BBTV)

<400> SEQUENCE: 57 tgacgt 6

<210> SEQ ID NO 58
<211> LENGTH: 6
<212> TYPE: DNA
<213> ORGANISM: Banana Bunchy Top Virus (BBTV)

<400> SEQUENCE: 58 acgtaa 6

<210> SEQ ID NO 59
<211> LENGTH: 5
<212> TYPE: DNA
<213> ORGANISM: Banana Bunchy Top Virus (BBTV)

<400> SEQUENCE: 59 ccacg 5

<210> SEQ ID NO 60
<211> LENGTH: 5
<212> TYPE: DNA
<213> ORGANISM: Banana Bunchy Top Virus (BBTV)

<400> SEQUENCE: 60 cgtgg 5

<210> SEQ ID NO 61
<211> LENGTH: 6
<212> TYPE: DNA
<213> ORGANISM: Banana Bunchy Top Virus (BBTV)

<400> SEQUENCE: 61 cacgtg 6

INTERGENIC REGIONS OF BANANA BUNCHY TOP VIRUS

FIELD OF INVENTION

This invention relates to DNA sequences of banana bunchy top virus (BBTV) and, in particular, to the intergenic regions of components 1 to 6.

BACKGROUND ART

Banana bunchy top disease (BBTD) is the most important virus disease of bananas (Dale, 1987, Advances in Virus Research 33 301–325), The disease is widespread in Asia and the South Pacific and has limited distribution in Australia and Africa. It has not been reported from the Americas. The disease was originally assumed to be caused by a luteovirus as it was persistently aphid transmitted but not mechanically transmitted, induced yellows type symptoms and infected plants that had damaged phloem. However, recently 18–20 nm isometric virus-like particles (VLPs) have been purified from infected plants and have been demonstrated to be associated with the disease (Harding et al., 1991, Journal of General Virology 72 225–230; Thomas & Dietzgen, 1991, Journal of General Virology 72 217–224; Wu and Su, 1990, Journal of Phytopathology 128 153–160). Harding et al (Harding et al., 1991, Journal of General Virology 72 225–230; Harding et al., 1993, Journal of General Virology 74 323–328) have isolated circular, single-stranded DNA of about 1 kb from these VLPs and cloned and sequenced one ssDNA component. This component, known as BBTV DNA component 1, had one large open reading frame (ORF) in the virion sense and encoded a putative replicase. This component was transmitted with the disease via aphids.

In Burns et al., 1994, Arch Virol. 137 371–380, they report the cloning and sequencing of a second component of BBTV. They found that a 93 nucleotide sequence was strongly conserved between the two ssDNA genomic components of BBTV. Two outwardly extending degenerate primers were designed from this sequence and used in a polymerase chain reaction (PCR) with DNA extracted from purified BBTV virions. PCR amplified products consisting of at least seven distinct bands all approximately 1 kb and possibly representing full-length BBTV dsDNA were resolved. The PCR amplified products were cloned and the clones screened by restriction enzyme analysis. Four distinct restriction analysis groups were identified. This reference concluded that the genome of BBTV contains at least five components and that BBTV belongs to a previously undescribed group of plant viruses which may also contain subterranean clover stunt virus.

In Karan et al., 1994, Journal of General Virology 75 3541–3546, mention is made of BBTV component 1 from isolates from 10 different countries being cloned and sequenced and the sequences were subsequently aligned and compared. This analysis indicated two groups: the South Pacific group (isolates from Australia, Burundi, Egypt, Fiji India, Tonga and Western Samoa) and the Asian group (isolates from the Philippines, Taiwan and Vietnam). The mean sequence difference within each group was 1.9 to 3.0% and between isolates from the two groups were approximately 10%, but some parts of the sequences differed more than others. However, the protein encoded by the major open reading frame differed by approximately 5%. The region from the beginning of the stem-loop sequence to the potential TATA box was identical in all isolates except for a two nucleotide change in the Western Samoan isolate and a single change in that of the NSW isolate. These results, together with other evidence, suggest that BBTV has spread to bananas after the initial movement of bananas from the Asian Pacific regions to Africa and the Americas.

In Xie et al., 1995, Phytopathology 85 339–347, the Hawaiian isolate of BBTV was purified from infected banana cultivar Williams. Three single-stranded DNA (ssDNA) components were cloned and sequenced; they were named component 1, 3 and 4 respectively. Component 1 is 1,110 nucleotides in length and shares 98% nucleotide sequence identity with the BBTV DNA component 1 of the Australian isolate as described In Harding et al. (1993) above. This component contains two open reading frames (ORF) capable of encoding a protein of 33.5 kDa, which may function as a replicase, and a protein about 15.2 kDa, with unknown functions. Component 3 is 1,057 nucleotides in length and does not contain any ORFs larger than 10 kDa. Component 4 is 1,017 nucleotides in length and potentially encodes a protein of 18.9 kDa. All three ssDNA components have a same stem-loop sequence and have a conserved non-coding region. The sequence of each of these-three components is different from that of BBTV DNA components of two Taiwanese isolates. BETV-specific clones were used in dot-blot hybridisation assays for detection of BBTV in plants using radioactive and non-radioactive probes. A polymerase chain reaction (PCR) assay was developed for detection of BBTV in banana samples and single aphids. Dot-blot hybridisation assays were as sensitive as enzyme-linked immunosorbent assay (ELISA) while PCR was 1,000 times more sensitive than dot-blot and ELISA assays for detection of BBTV in bananas.

Although so called intergenic regions of genomic components 1, 3 and 4 have been detected in Harding et al., 1993 supra; and Xie and Hu, 1995, supra, the only charcteristic of such intergenic regions has been a stem-loop structure in component 1 as disclosed in Harding et al., 1993, supra.

In an earlier application, (i.e. International Application PCT/AU95/00311) reference is made to BBTV components 3, 4 and 6 which are claimed per se. Regions outside the ORF regions (i.e. the so called "intergenic regions") have also been disclosed in this earlier application. Genomic components 1, 3 and 4 disclosed in Xie and Hu, 1995, supra correspond to components 1, 2 and 5 referred to in the earlier application PCT/AU95/00311.

SUMMARY OF THE INVENTION

Surprisingly, it has now been discovered that intergenic regions of BBTV genomic components 1–6, or parts thereof, have sequences derived therefrom capable of promoting, enhancing, regulating or modifying transcription of non-BBTV genes.

The invention therefore includes within its scope, the aforementioned intergenic regions when used for promoting, enhancing, regulating or modifying transcription of a non-BBTV gene as well as parts thereof, sequences derived therefrom and mutants thereof per se.

The invention also includes within its scope a DNA molecule which is a partial fragment of an intergenic region of a BBTV component or alternatively which DNA molecule is derived from said intergenic region whereby the DNA molecule is capable of promoting, enhancing, regulating or modifying transcription of a non-BBTV gene.

The partial fragment is defined in this specification as being a sequence less than the full sequence of the intergenic region of a BBTV component but equal to or greater than a sequence of approximately 172 base pairs from a BBTV component. The sequence of said DNA molecule may be identical to the complementary sequence of the partial fragment of an intergenic region of a BBTV component.

The intergenic region is used in this specification to define the non-coding region of a BBTV component or the region outside the ORF in a BBTV component.

The sequence of the DNA molecule may be substantially identical or substantially complementary to the partial fragment of the intergenic region of BBTV components 1–6. Substantially is used in this specification to refer to sequences having variations up to 20%. The amount of sequence variation can be determined by standard hybridisation procedures or sequence comparison. The percentage of 20% is the variation shown with the region outside of the ORF of component 1 between different geographical isolates (Karan et al., 1994, Journal of General Virology, 75, 3541–3546; and U.S. patent application Ser. No. 08/202186). Both of these documents are herein incorporated by reference to support the claim of 20% variation of all components of BBTV. The variation determined for component 1 of different geographical isolates is representative of the variation between each component from different geographical isolates. Thus variation up to 20% also applies to the sequences of components 2 through to 6 discussed below.

The term derived defines any sequence that has been changed, altered or modified by whatever procedure including mutagenesis from a fragment of the intergenic region of a BBTV component.

In particular, the sequence of the DNA molecule may be the BBTV intergenic region derived inserts of pBT6.1 (approximately 623 base pair fragment), pBT6.2 (approximately 351 base pair fragment), pBT6.3 (approximately 239 base pair fragment), and pBT6.4 (approximately 172 base pair fragment) from component 6; pBT1.1 (approximately 214 base pair fragment), pBT1.INT (approximately 980 base pair fragment) from component 1; pBT2.1 (approximately 855 base pair fragment) from component 2; pBT3.1 (approximately 526 base pair fragment) from component 3; pBT4.1 (approximately 659 base pair fragment) from component 4; and pBT5.1 (approximately 454 base pair fragment) from component 5. The DNA molecule may be 275 base pair region which includes the CR-M that is present in the insert of pBT6.1 but not in the insert of pBT6.2. The 275 base pair region may be a regulatory region. The DNA molecule may comprise the region between or including the CRSL region and the ATG of the open reading frame of any one of the BBTV components 1 to 6. The inserts of pBT1.1, pBT2.1, pBT3.1, pBT4.1, pBT5.1 and pBT6.1 are shown in FIG. 11. FIG. 12 shows the sequence of the insert of pBT1.INT. FIG. 13 shows the DNA sequence of the inserts of (a) pBT6.1; (b) pBT6.2; (c) pBT6.3; and (d) pBT6.4.

The non-BBTV gene may be any suitable gene such as GUS, NPTII, insecticide resistance gene, herbicide resistance gene or a growth promoting gene.

The DNA molecule may transcribe the gene in any suitable prokaryote or eukaryote host. Preferably, the DNA molecule may transcribe the gene in a monocotyledon plant cell such as plant cells from Musa spp (banana), wheat cells. The DNA molecule may transcribe the gene in a monocotyledon plant such as banana and wheat. Preferably the DNA molecule may transcribe the gene in a dicotyledon plant cell such as tobacco and zucchini cells. The DNA molecule may transcribe the gene in a dicotyledon plant such as tobacco and zucchini. The DNA molecule preferably transcribes the gene in cells of undifferentiated tissue in a dicotyledon plant.

In a second aspect, the invention is a DNA chimaeric vector or cassette having a DNA molecule as described above upstream of a gene of interest to enable the promoting, enhancing, regulating or modifying of transcription of the gene.

The chimaeric vector may be derived from pBI101.3. The vector may be any suitable construct mentioned below. The cassette may be any suitable construct mentioned below. The gene of interest may be any suitable gene as mentioned above. The chimaeric vector or cassette may be introduced into any suitable host including monocotyledon plant cells and dicotyledon plant cells for expression in the host.

The invention in a third aspect is a plant cell having a DNA molecule as described above.

The invention in a fourth aspect is a plant with the plant cells as described above.

The invention in a fifth aspect provides a method of expressing a non-BBTV gene in a plant cell using the DNA molecule as described above.

The invention will now be described with reference to preferred embodiments. However, these preferred embodiments are given by way of example. Example 1 describes the discovery and identification of the further three components of BBTV and is incorporated in the specification for convenience to allow a man skilled in the art to isolate these BBTV components. This information has essentially been published in Burns et al., 1995, Journal of General Virology, 76, 1471–1482).

BRIEF DESCRIPTION OF THE DRAWINGS

FIGS. 1A–1E are representations of the nucleotide sequences of BBTV DNA components 2, 3, 4, 5, and 6 (SEQ ID NOs:1, 2, 4, 6, and 8, respectively), and the deduced amino acid sequences (SEQ ID NOs: 3, 5, 7, and 9 for components 3, 4, 5, and 6, respectively) of the major ORFs. The representations for components 2, 3, 4, 5, and 6 are given in FIGS. 1a, 1b, 1c, 1d, and 1e, respectively. The potential TATA boxes are in bold and double underlined; the potential polyadenylation signals are in bold and underlined; the stem-loop structure is in italics and underlined, with the stem sequence arrowed; the CR-SL is underlined; the CR-M is in bold and italics; and the ORF is in bold.

FIG. 3 is an alignment of the stem-loop regions (CR-SL) of BBTV DNA components 1 to 6 (SEQ ID NOs: 10–15, respectively). The stem-loop structure in each component is underlined and the loop sequence is in italics. Asterisks indicate nucleotides that are conserved between all components. Dots indicate gaps in some sequences for maximising sequence alignment.

FIG. 4 is an alignment of the major common regions (CR-M) of BBTV DNA components 1 to 6 (SEQ ID NOs:16–21, respectively). The 15 nucleotide GC-rich sequence is underlined. Asterisks indicate nucleotides that are conserved between all components and diamonds indicate nucleotides that are conserved between components 2 to 6 in the first 26 nucleotides covering the deletion in component 1. Dots indicate gaps in some sequences for maximising sequence alignment, and the imperfect repeat sequences are shown in italics.

FIG. 11 is a nucleotide sequence alignment of the intergenic regions of components 1 to 6 of BBTV (SEQ ID NOs:22–27, respectively). bbtvpro1 is the insert of pBT1.1; bbtvpro2 is the insert of pBT2.1; bbtvpro3 is the insert of pBT3.1; bbtvpro4 is the insert of pBT4.1; bbtvpro5 is the insert of pBT5.1; and bbtvpro6 is the insert of pBT6.1. Note in bbtvpro1 that Adh1 US1 is present at position 1004. With respect to bbtvpro2 note that TGA-1b is present at positions 952 and 1053; Adh1 US3 is present at position 137; and G-BOX is present at position 225. With respect to bbtvpro3 note Adh1 US1 is present at position 1069. With respect to bbtvpro4 note that TGA-1b is present at position 182; ADh1 US1 is present at position 1037; and G-BOX is present at positions 45, 63, 128 and 148. With respect to bbtvpro5 note that TGA-1b is present at position 96; Adh1 US1 is present at position 1012; and G-BOX is present at positions 45 and 64. With respect to bbtvpro6 note that TGA-1a is present at position 1083; TGA-1b is present at position 44; Adh1 US1 is present at position 173; and G-BOX is present at position 46. Also note that the G-BOX is a plant promoter motif which is associated with the transcription core sequence: CACGTG.

FIG. 12 is the DNA sequence of the insert of pBT1.INT (982 base pair; SEQ ID NO:28). Note that the sequence of the intergenic region of BBTV component 1 is based on the small open reading frame.

FIGS. 13A–13D are the DNA sequence of the inserts of pBT6.1 (622 base pair; SEQ ID NO:29; FIG. 13*a*), pBT6.2 (351 base pair; SEQ ID NO:30; FIG. 13*b*), pBT6.3 (238 base pair; SEQ ID NO:31; FIGS. 13*c*), and (*d*) pBT6.4 (182 base pair; SEQ ID NO:32; FIG. 13*d*). Note that the bolded region in pBT6.3 is the sequence associated with the majority of promoter activity of the component 6 intergenic region. This region is removed in pBT6.4.

DETAILED DESCRIPTION OF THE INVENTION

EXAMPLE 1

BBTV Components

Methods

Synthesis and cloning of cDNA. Bananas with characteristic symptoms of banana bunchy top disease were collected from the Nambour region of S-E Queensland. BBTV particles were purified as described by Wu & Su, 1990, Journal of Phytopathology 128 153–160 and Thomas & Dietzgen, 1991, Journal of General Virology 72 217–224. Nucleic acid was extracted from virions as described by Francki & Randles, 1973, Virology 54 359–368. Double stranded DNA was synthesised as described by Gubler & Hoffman, 1983, Gene 25 263–269 using random hexamers (Bresatec) to prime first strand synthesis. The dsDNA was treated with mung bean nuclease (Promega) and ligated into SmaI digested plasmid vector pUC18 (Upcroft & Healey, 1987, Gene 51 69–75). The plasmid was then used to transform *Escherichia coli strain JM*109 (Hanahan, 1983, Journal of Molecular Biology 166 557–580) and potential recombinant clones were identified by screening on X-gal substrate (Vieira & Messing, 1982, Gene 19 259–268)

Figure 2A:
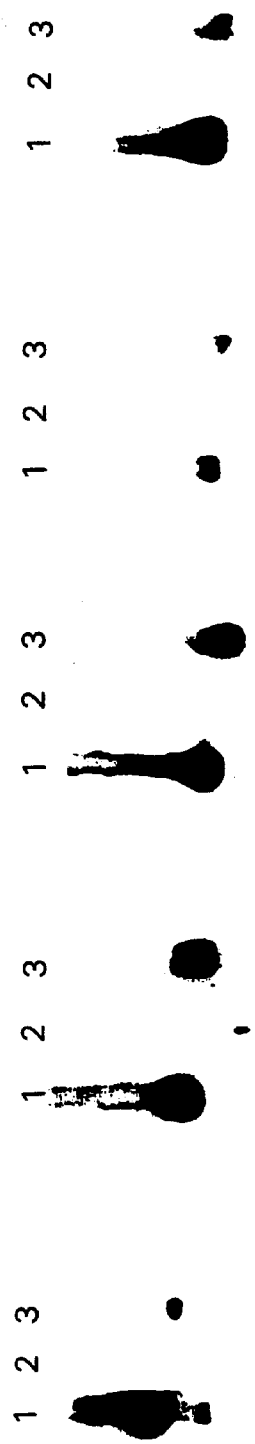
FIG. 2A–2B are autoradiograms of blots. Each blot was separately probed with either $^{32}$P-labelled oligonucleotides (component 2) or full length RNA transcripts (components 3 to 6) specific for the virion- or complementary-sense strands of each respective component. Panel (a) blots were hybridised with probes complementary to the component sequences presented in FIGS. 1a–1e. Panel (b) blots were hybridised with probes having the same sequences presented in FIGS. 1a–1e. Lane 1: full length clone of each respective component. Lane 2: healthy banana nucleic acid. Lane 3: DNA extracted from purified BBTV virions.
Figure 2B:
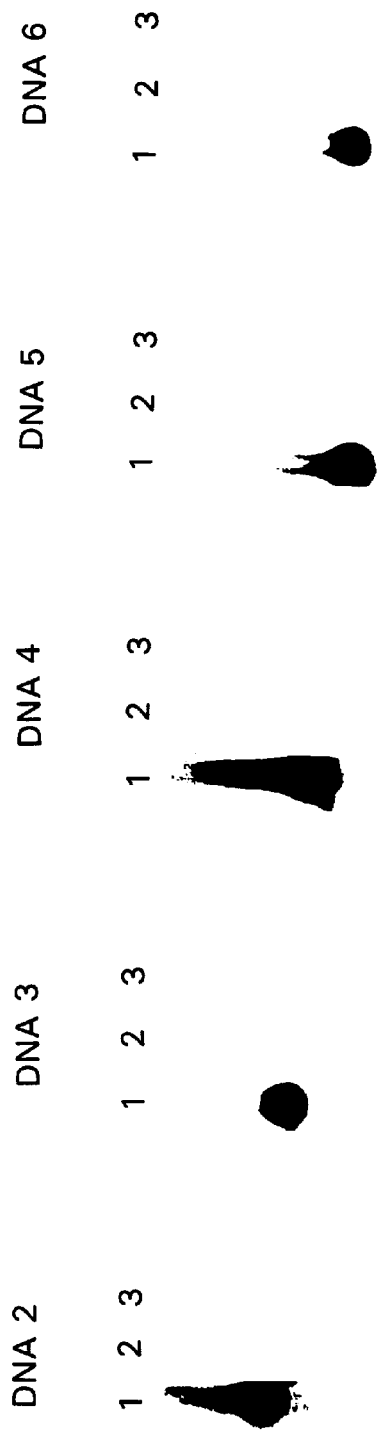

Plasmids were isolated using the alkaline lysis method (Sambrook et al., 1989, Molecular Cloning: A Laboratory Manual. New York: Cold Spring Harbor Laboratory). Inserts were excised by digestion with EcoRI/HindIII, electrophoresed in agarose gels and capillary blotted onto Hybond N+ (Amersham) using 0.4 M NaOH (Sambrook et al., 1989, Molecular Cloning: A Laboratory Manual. New York: Cold Spring Harbor Laboratory). Inserts for use as DNA probes were purified from agarose gels using a Gene-Clean kit (Bresatec). DNA probes were labelled using a Ready-To-Go labelling kit (Pharmacia) as recommended by the manufacturer. Prehybridisations and hybridisations were done as described by Burns eta., 1994, Archives of Virology 137 371–380.

Sequencing and sequence analysis. Mini preparations of respective BBTV clones were prepared by alkaline lysis followed by polyethylene glycol precipitation (Hattori & Sakaki, 1986, Analytical Biochemistry 162 232–238). Sequencing was done using $^{35}$SdATP and a Sequenase kit (US Biochemicals) as recommended by the manufacturer. Reaction products were electrophoresed in 8% (w/v) polyacrylamide gel containing 7 M urea. Gels were fixed, dried and exposed to X-ray film. Primers used for sequencing were either universal sequencing primers or 17–30 nt primers complementary to appropriate regions of the cloned viral DNA synthesised using an Applied Biosystems (ABI) PCR Mate and processed as recommended by the manufacturer.

PCR products for sequencing were purified from agarose gels using a Gene-Clean kit (Bresatec). DNA was sequenced using a Sequenase kit (USB) essentially as described by the manufacturer. Denaturation of template DNA (500 ng) was done by boiling following the addition of DMSO and 3 pmoles of sequencing primer.

Nucleotide sequences were analysed using the GCG analysis package version 8 available through the ANGIS computing facility at the University of Sydney, Australia. Nucleotide and amino acid sequences were aligned using the Clustal V software package (Higgins et al., 1991, CABIOS 8 189–191). Four DNA databases (GenBank, GenBank Weekly Updates, EMBL and EMBL weekly updates) and five protein databases (SwissProt, SwissProt Weekly Updates, PIR, GenPeptide Proteins and GenPeptides Weekly Updates) were searched for sequence homologies with BBTV nucleotide and deduced amino acid sequences using two database search analysis programs, FASTA (Pearson & Lipman, 1988, Proceedings of the National Academy of Sciences, U.S.A. 85 2444–2448) and BLAST (Altschul et al., 1990, Journal of Molecular Biology 215 403–410).

PCR: Analysis and cloning. Using the respective nucleotide sequences of clones (I) pBTRP-11, 20, 80 and 88 and (ii) pBTRP-P1 and P2 and the nucleotide sequences of BBTV components 1 (Harding et al., 1993, Journal of General Virology 74 323–328) and 2, three sets of immediately adjacent outwardly extending primers ((I) primer A: 5' GCATCCAACGGCCCATA 3'(SEQ ID NO:33); primer B: 5'CTCCATCGGACGATGGA 3'(SEQ ID NO:34); (ii) primer C: 5' TATTAGTAACAGCAACA 3'(SEQ ID NO:35); primer D: 5' CTAACTTCCATGTCTCT 3'(SEQ ID NO:36); (iii) primer E: 5' CGGGa/tATa/cTGATTGt/gGT 3'(SEQ ID NO:37); and primer F: 5' TACa/tTTTGTCATAGc/tGT 3'(SEQ ID NO:38)) were synthesised and used in a PCR with BBTV DNA as template as described by Burns et al., 1994, Archives of Virology 137 371–380). The amplified products were cloned using the TA cloning kit (Invitrogen) into the plasmid vectors pCRII or pCR2000 as recommended by the manufacturer or into T-tailed pUC19 and Bluescript (Marchuk et al., 1990, Nucleic Acids Research 19 1154). Recombinant clones were selected using X-gal substrate on Luria Bertani (LB) agar containing the appropriate antibiotic and plasmids isolated using the alkaline lysis method (Sambrook et al., 1989, Molecular Cloning: A Laboratory Manual. New York: Cold Spring Harbor Laboratory). Clones with apparent full-length inserts (approximately 1 kb) were selected for sequencing.

Polarity of virion ssDNA. BBTV ssDNA was extracted, electrophoresed in agarose and capillary blotted onto duplicate nylon membranes (Harding et al., 1993, Journal of General Virology 74 323–328). For component 2, a DNA 3'-end labelling kit (Boehringer Mannheim) was used to prepare $^{32}$P-labelled strand specific oligonucleotide hybridisation probes (primer BT2F5.30 (G): 5' GGTCCCCTTTAA-GATTCCTTTCTTCGTCGC 3'(SEQ ID NO:39); primer BT2R5.30 (H): 5' CGGAAAATGAATAAGTATGAGGT-GAAAGAG 3'(SEQ ID NO:40)). Membranes were prehybridised and hybridised for 12 and 20 hours respectively in Rapid-hyb (Amersham) at 60° C. Filters were washed once with 1% SDS, 2×SSC (0.3 M NaCl, 0.03 M sodium citrate, pH 7.0) at room temperature followed by washes with 2×SSC at 65° C. Dried membranes were exposed to x-ray film at −80° C. using intensifying screens.

For components 3, 4, 5 and 6, strand-specific RNA probes were used. Full-length RNA transcripts of full-length BBTV clones of each of the four components were synthesised using a riboprobe in vitro transcription kit (Promega) as recommended by the manufacturer.

Results

Cloning and Sequencing of Five Genomic Components

Five new genomic components of BBTV were cloned and sequenced from two libraries, (I) a random primed library and (ii) aPCR library.

(I) Random Primed Library

A random primed library was generated from BBTV ssDNA extracted from purified virions. The resultant dsDNA was treated with mung bean nuclease, blunt-end ligated into SmaI cut pUC18 and cloned into E. coli JM109. This library was screened with $^{32}$P-labelled DNA from BBTV virions, healthy bananas and the insert from pBT338 which was a partial clone of BBTV DNA component 1 (Harding et al., 1991, Journal of General Virology 72 225–230; Harding et al., 1993, Journal of General Virology 74 323–328).

BBTV DNA Component 2: Four clones, pBTRP-11, 20, 80 and 88, hybridised with BBTV virion DNA and with each other but not with healthy banana DNA or pBT338. The inserts from these clones were sequenced; pBTRP-20 and 88, each with inserts of 220 bp, had identical sequences; pBTRP-80 had an insert of 188 bp and had 148 bp sequence identical to pBTRP-20 and 88 and a further 40 bp sequence at one end that was unique; the sequence of the 115 bp insert of pBTRP-11 was identical to the equivalent region of pBTRP-20 and 88. Two immediately adjacent, outward extending primers, primers A and B, were designed from the overlapping sequence of the four clones such that these primers would prime the amplification of full length dsDNA copies of a circular ssDNA molecule (Harding et al., 1993, Journal of General Virology 74 323–328). BBTV virion ssDNA was amplified by PCR using these primers and Pfu DNA polymerase and the product cloned into pCR2000. Four of the resultant clones were sequenced in both directions using universal forward and reverse primers and sequence specific primers. Three of these clones contained 1060 bp inserts and one clone contained a 1059 bp insert. The four clones had identical sequences except for nine single nucleotide changes including one deletion. Further, the sequences of the original four cDNA clones were found within the four PCR clones. The consensus sequence of this component, termed BBTV DNA component 2, was compiled (FIG. 1a) and compared with the sequence of BBTV DNA component 1 (Harding et al., 1993, Journal of General Virology 74 323–328); the two sequences were essentially different apart from two significant regions of homology.

BBTV DNA Component 6: A further two clones from the same random primed library, pBTRP-P1 and P2, also hybridised with labelled BBTV virion DNA but not with DNA from healthy bananas or pBT338. However, the inserts of these clones, both of approximately 1 kb, were digested with EcoRV whereas neither components 1 nor 2 had EcoRV sites. The two clones were partially sequenced using universal forward and reverse primers. The sequences of both clones were identical but clearly different to those of components 1 and 2. Again, two immediately adjacent, outwardly extending primers, primers C and D, were designed from the sequence and synthesised. BBTV virion ssDNA was used as a template with these two primers in a PCR reaction and the resultant product cloned into a T-tailed Bluescript vector. One apparent full length clone, pBT-P2A1, was selected and sequenced in both directions from subclones generated by exonuclease III digestion and universal forward and reverse, and sequence-specific primers. The final component 6 sequence of 1089 bp was then compiled (FIG. 1e)

(ii) PCR Library

When the sequences of components 1 and 2 were compared, two regions of homology were identified. The first region, later defined as the stem-loop common region (CR-SL) included the potential stem/loop sequence previously identified in component 1 (Harding et al., 1993, Journal of General Virology 74 323–328); the second region, which was contained within the region later defined as the major common region (CR-M), was a sequence of approximately 66 nucleotides 5' to the stem-loop sequence. It was hypothesised that all BBTV genomic components should contain a CR-M and therefore two immediately adjacent, outwardly extending degenerate primers, primers E and F, were designed from this region, synthesised and extended by PCR using BBTV virion ssDNA as a template (Burns et al., 1994, Archives of Virology 137 371–380). Seven products, each of approximately 1 kb, were resolved by polyacrylamide gel electrophoresis. The products were cloned into pCRII. The resultant clones were divided into three groups, groups B, C and D, on the basis that they hybridised with BBTV virion DNA but not DNA from healthy bananas and that each group had restriction patterns different to the other two groups and to components 1, 2 and 6 (Burns et al., 1994, Archives of Virology 137 371–380). One group, group A, had a restriction pattern indistinguishable from that of component 2 and it was later confirmed by sequencing that group A clones represented clones of component 2.

Each group of clones was assumed to represent a new and unique BBTV DNA component. For each group of clones, three clones (component 3) or four clones (components 4 and 5) were partially sequenced using universal forward and reverse primers. In each instance, all the clones within a group had identical sequences where these sequences overlapped except for one or two single nucleotide changes. Further, the sequences from each group were different to each other group and to the sequences of components 1, 2 and 6. One clone from each group or component was selected and fully sequenced in both directions. Importantly, each of these groups of clones were generated using degenerate primers covering a sequence of 34 nucleotides derived from the conserved CR-M of components 1 and 2. The CR-M from components 1 and 2 was not fully conserved and thus it was expected that the hypothesised CR-M sequence would vary between other components. Therefore, converging primers unique to each component were designed and used to amplify a sequence including CR-M for each component from BBTV virion ssDNA. The resultant PCR product was sequenced directly using the two component specific converging primers.

BBTV DNA Component 3: Component 3 (Group C clone pBTP-64) was sequenced in both directions from the original clone and from subclones generated by exonuclease III digestion or restriction fragments using universal forward and reverse primers and three sequence-specific primers. Two additional converging primers were designed from this sequence to amplify a 380 bp product including the CR-M. The sequence of this product was identical to that of pBTP-64 except for five single nucleotide changes, four of which were in the sequence covered by the original degenerate primers and one outside this sequence at nucleotide 947. The final component 3 sequence of 1075 bp was then compiled (FIG. 1*b*).

BBTV DNA Component 4: Component 4 (Group D clone pBTP-62) was sequenced in both directions from the original clone and from subclones generated by exonuclease III digestion using universal forward and reverse primers and three sequence-specific primers. Two additional converging primers were designed from this sequence to amplify a 350 bp product including the CR-M. The sequence of this product was identical to that of pBTP-62 except for two single nucleotide changes in the sequence covered by the original degenerate primers. The final component 4 sequence of 1043 bp was then compiled (FIG. 1*c*).

BBTV DNA Component 5: Component 5 (Group B clone pBTP-129) was sequenced in both directions from the original clone and from subclones generated by exonuclease III digestion using universal forward and reverse primers and three sequence-specific primers. Two additional converging primers were designed from this sequence to amplify a 290 bp product including the CR-M. The sequence of this product was identical to that of pBTP-129 except for four single nucleotide changes in the sequence covered by the original degenerate primers. The final component 5 sequence of 1018 bp was then compiled (FIG. 1*d*).

Orientation of Genomic Components and Association With Banana Bunchy Top Disease We have previously shown that the BBTV genome is encapsidated as single-stranded DNA (Harding et al., 1991, Journal of General Virology 72 225–230; Harding et al., 1993, Journal of General Virology 74 323–328). To determine the orientation of each component in virions, strand-specific DNA or RNA probes specific for each component were synthesised and hybridised with BBTV virion DNA. Component 2 specific probes were two 3' end-labelled 30mer oligonucleotides whereas probes specific for components 3, 4, 5 and 6 were SP6, T3 or T7 promoted $^{32}P$-labelled RNA transcripts. For each component, the probes whose sequences were complementary to the component sequences presented in FIG. 1 hybridised strongly to BBTV virion DNA whereas the probes whose sequences were the same as the FIG. 1 sequences did not hybridise (FIG. 2). This indicated that each component was encapsidated as ssDNA and only in one orientation, that presented in FIG. 1.

Further, the strand- and component-specific probes that hybridised with BBTV virion ssDNA were used as probes to demonstrate that each component was associated with banana bunchy top disease. Plant DNA extracts from three (for component 2) or four (for components 3 to 6) different BBTV isolates and DNA from four healthy bananas was Southern blotted and hybridised with each probe. Each component-specific probe hybridised with a low molecular weight DNA of expected size in all the extracts from BBTV-infected bananas but did not hybridise with the extracts from healthy bananas (results not shown). This indicated that each component was clearly associated with the disease and the virus.

Analysis of the BBTV Genomic Components

The sequences of the five BBTV genomic components presented here and the sequence of component 1 (Harding et al., 1993, 2) were aligned and compared. Each of the six sequences were different except for two significant regions which had varying degrees of homology between all six components.

Stem-loop common region: We have previously identified a potential stem-loop structure in BBTV component 1 (Harding et al, 1993, Journal of General Virology 74 323–328) which had a loop sequence almost identical to the invariant loop sequence of geminiviruses (Lazarowitz, 1992, Critical Reviews in Plant Sciences 11 327–349). An equivalent stem/loop structure was also found in components 2 to 6 (FIG. 3). Each component had an 11 nucleotide loop sequence of which 9 consecutive nucleotides were conserved between all components. Each component also had a 10 bp stem sequence of which 14 nucleotides were fully conserved. However, when all six components were compared, the region of homology extended up to 25 nucleotides 5' of the stem-loop structure and up to 13 nucleotides 3' of the stem/loop structure. The 5' 25 nucleotides were fully conserved between components 1, 3, 4 and 5. There were apparently two deletions in both components 2 and 6. In component 2, eight nucleotides were fully conserved with components 1, 3, 4 and 5 whereas in component 6, 16 nucleotides were conserved with these other components. The 13 nucleotides 3' of the stem-loop were fully conserved between all six components except for an apparent single nucleotide deletion in component 2. The sequence of up to 69 nucleotides including the stem-loop sequence was termed the stem-loop conserved region or CR-SL.

Major common region: The second common region was located at various distances 5' of the CR-SL and was called the Major Common Region or CR-M. This region varied in size from 65 nucleotides in component 1 to 92 nucleotides in component 5 (FIG. 4). Component 1 apparently had the first 26 nucleotides of the CR-M deleted as well as a further single nucleotide deletion. Components 2, 3 and 4 had two single nucleotide deletions and component 6 had one single nucleotide deletion. Forty-five nucleotides were conserved between all components and 23 of the first 26 nucleotides, deleted in component 1, were conserved between components 2 to 6. Also in components 2 to 6, there was an almost complete 16 nucleotide direct repeat (ATACAAc/gACa/gCTATGA(SEQ ID NO:54)) from nucleotides 4 to 20 and 21 to 36. Further, a 15 nucleotide GC rich sequence (average of 86% GC) was located from nucleotides 78 to 92 and was 93% conserved between all components.

Figure 5:
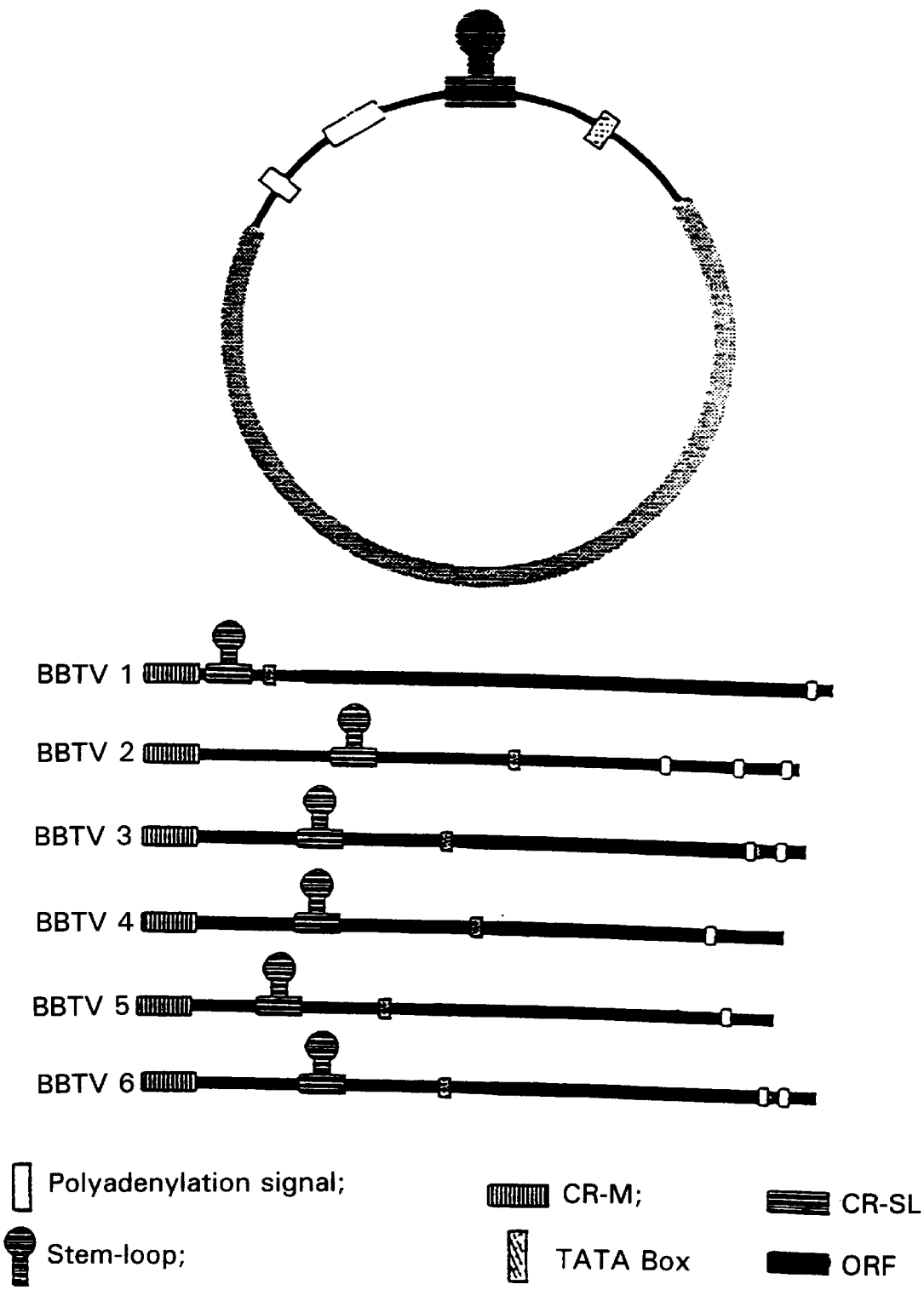
FIG. 5 is a diagrammatic representation of the proposed genomic organisation of BBTV showing (i) the general organisation of all components and (ii) a linear representation of each component.
Figure 6:
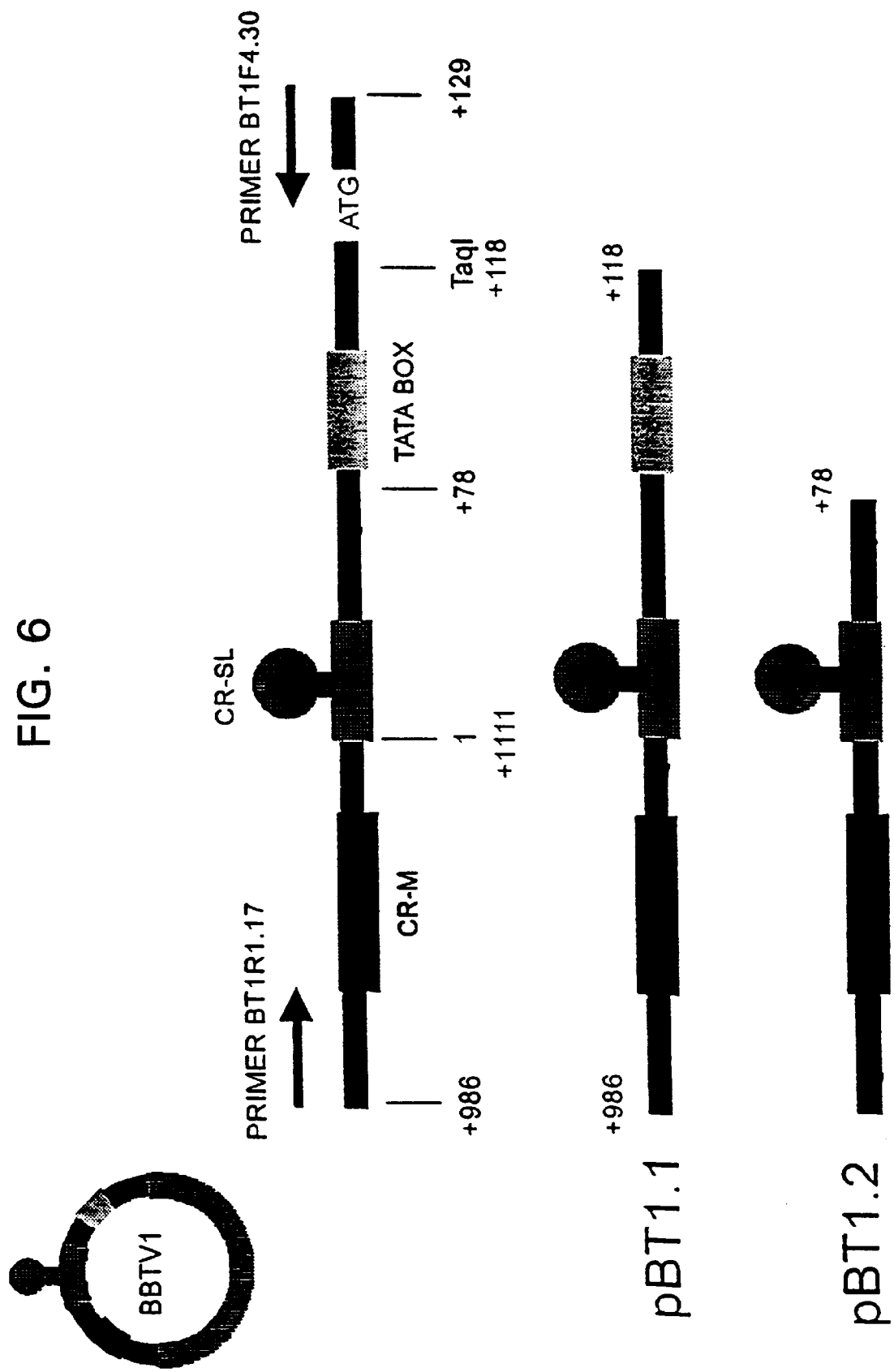
FIG. 6 is a diagrammatic representation of various constructions of the intergenic region of component 1.
Figure 7:
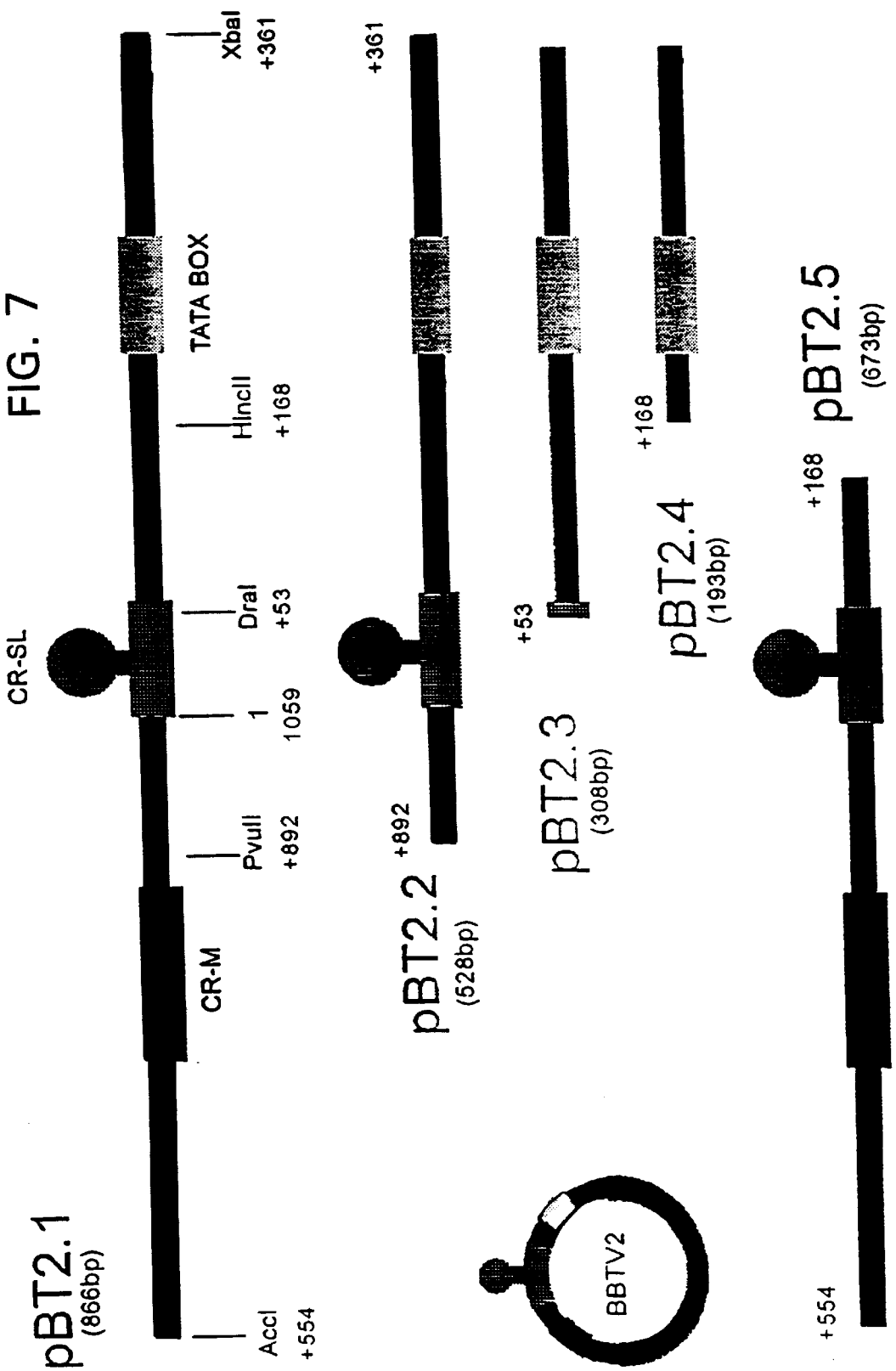
FIG. 7 is a diagrammatic representation of various constructions of the intergenic region of component 2.

The sequence between the last nucleotide of the CR-M and the first nucleotide of the CR-SL varied in length from 22 nucleotides in component 1 to 233 nucleotides in component 2 (FIGS. 1 and 5). Interestingly, this sequence of 175 nucleotides in components 3 and 4 was 97% conserved between these two components.

Pontential TATA boxes: A potential TATA box was identified in BBTV component 1 and was located 20 nucleotides 3' of the last nucleotide of the stem-loop and 43 nucleotides 5' of the start codon of the putative replicase gene (Harding et al., 1993, Journal of General Virology 74 323–328). Similar potential TATA boxes were also identified in components 2 to 6. In each of these components, the potential TATA box was a nine nucleotide sequence, CTATa/ta/tAt/aA(SEQ ID NO:55) and was located downstream from the stem-loop sequence (FIG. 1). However, the sequence between the last 3' nucleotide of the stem-loop sequence and the potential TATA box was considerably longer in components 2 to 6 than in component 1 and varied from 157 nucleotides in component 5 to 227 nucleotides in component 4 (FIGS. 1 and 5).

Analysis of Potential Polyadenylation Signals

Six potential polyadenylation signals were identified associated with the 3' end of the major ORFs of components 3 to 6. A GT-rich region of 10 to 17 nucleotides was located between 0 and 23 nucleotides 3' of each of these polyadenylation signals and each GT-rich region contained the trinucleotide sequence TTG (FIG. 4). Only one potential polyadenylation signal identified in component 2 had a corresponding GT-rich region with the trinucleotide sequence TTG and this was located 233 nucleotides 3' of the nonanucleotide potential TATA box in the virion sense.

Conclusions

All six components share two common regions, the CR-SL and the CR-M, in the putative intergenic or untranslated region and five of the six components had one large ORF in the virion sense with associated potential TATA boxes and polyadenylation signals (FIG. 5). The CR-SL incorporated the conserved stem-loop structure. The loop sequence of 11 nucleotides was conserved in all BBTV components with the exception of two nucleotides and was similar to that present in nine geminiviruses (Lazarowitz, 1992, Geminiviruses: genome structure and gene function. 2), CFDV (Rohde et aL, 1990. Virology 176 648–651) and a further BBTV component (Yeh et al., 1994, Virology 198 645 652. A model for implicating the loop sequence in rolling circle replication has been described for geminiviruses (Saunders et al., 1993, DNA forms of the geminivirus—African cassava mosaic virus—consistent with the rolling circle mechanism of replication. IXth International Congress of Virology, Glasgow, August, 1993. Abstract P60-18). It is possible that the loop sequence in BBTV has a similar function. The stem-loop sequences were also highly conserved in all BBTV components and contained the pentanucleotide sequence TACCC which has been shown to be the site for initiation of viral strand DNA synthesis in wheat dwarf geminivirus (Heyraud et al., 1993, EMBO Journal 12 4445–4452).

The major common region (CR-M) was identified in all components and was located 3' of the major ORF (except for component 2 where no major ORF was identified) and 5' of the CR-SL (FIG. 5). Hexanucleotide repeats were identified within the CR-M in all components except that of component 1. However, no function could be directly attributed to these repeats but they may be associated with, or part of promoter sequences. The CR-M also contained a 15 nt GC-rich sequence located at the 3' end and had the potential to form a small stem-loop structure. This GC-rich sequence also contained two direct GC-repeats which resembled the Sp1 binding sites found in promoters of genes in animal cells and viruses (Fenoll et al., 1990, Plant Molecular Biology 15 865–877). A similar promoter in the monocot-infecting maize streak geminivirus has been shown to be required for maximal rightward transcription and also appeared to bind maize nuclear factors in a non-cooperative manner (Fenoll et al, 1990, Plant Molecular Biology 15 865–877).

Karen et al., 1994, Journal of General Virology 75 3541–3546, reported that the component 1 CR-M sequence was highly conserved within the "South Pacific" group of BBTV isolates (96.5% homology) and within the "Asian" group of isolates (98.0% homology) but was highly variable between the two groups of isolates (68.0% homology). There was 76% between the CR-M sequences of the six different components of an Australian isolate reported here. Therefore, it will be important to determine the level of homology between the CR-M sequences of individual components from the different groups of isolates to see whether these sequences are highly conserved within groups of isolates but variable between groups and different components and further whether this has any biological significance.

The nucleotide length and sequence between the CR-M and CR-SL was dissimilar in four of the six components. However, in components 3 and 4, this 175 nucleotides region was 97% homologous and the 334 nucleotides from the 5' end of the CR-M to the 3' end of the CR-SL were 98% homologous. A similar large common region of 300 nucleotides has been found in geminiviruses and is identical between the A and B components of individual bipartite geminiviruses (Lazarowitz, 1992, Geminiviruses: genome structure and gene function. 2). In geminiviruses, this region included the stem-loop region. A region of homology was also found in five of the seven components of SCSV which included the stem-loop region (Surin et al., 1993, The subterranean clover stunt virus genome consists of microchromosomes encoding single ORFs. IXth International Congress of Virology, Glasgow, August, 1993. Abstract P62-1) which is similar to the geminiviruses but different to four of the six BBTV components.

Figure 8:
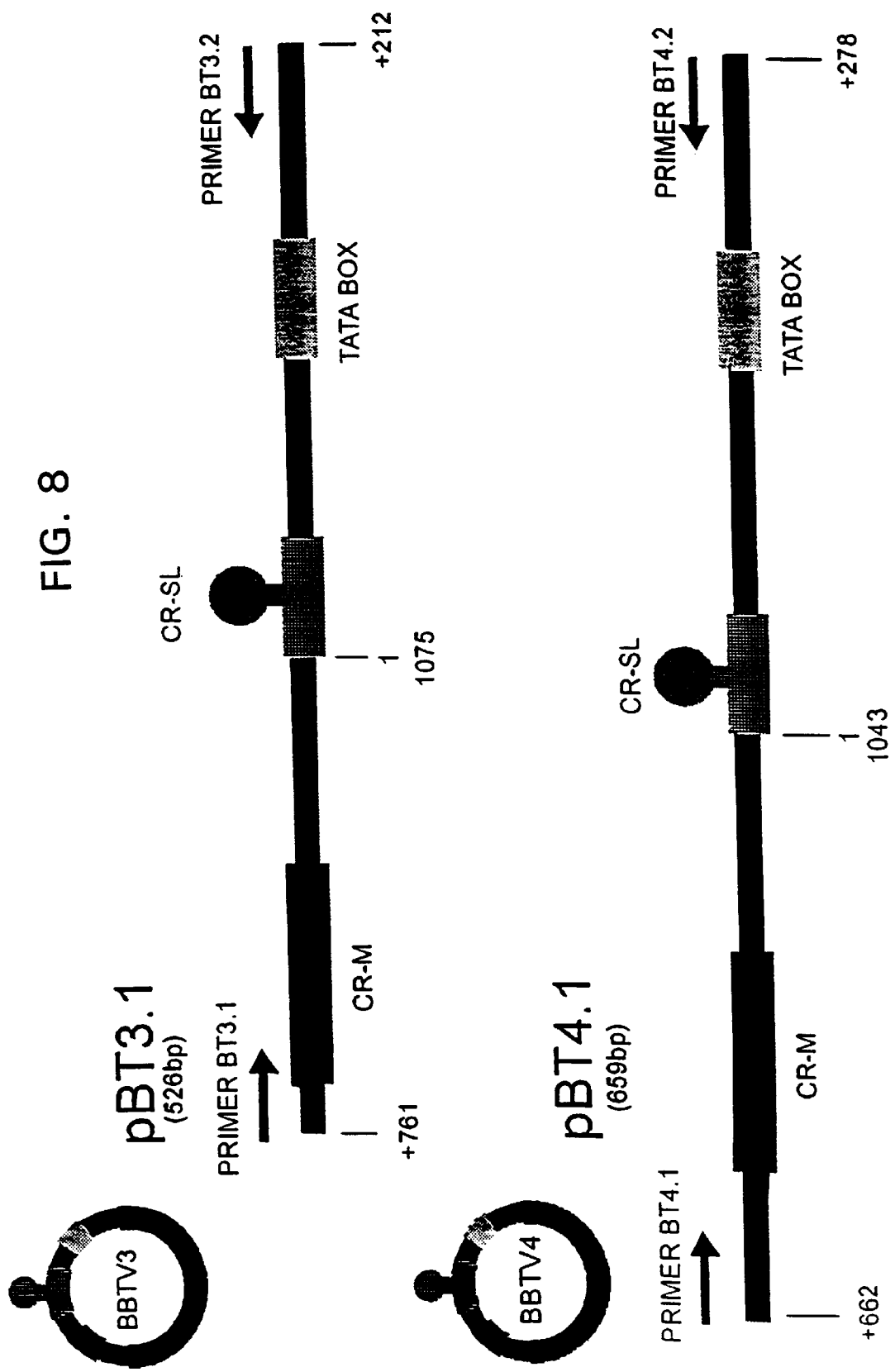
FIG. 8 is a diagrammatic representation of various constructions of the intergenic region of components 3 and 4.
Figure 9:
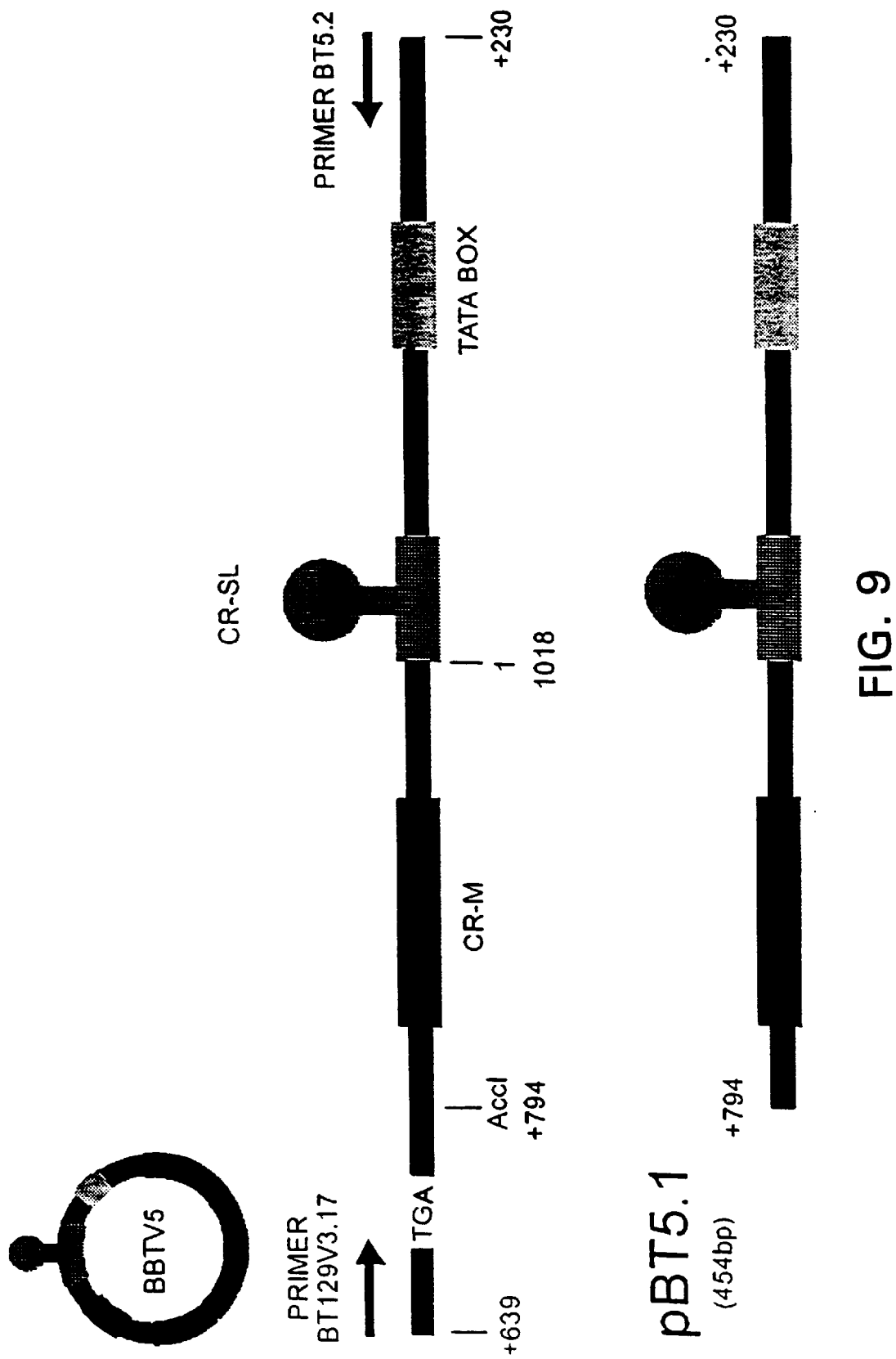
FIG. 9 is a diagrammatic representation of various constructions of the intergenic region of component 5.
Figure 10:
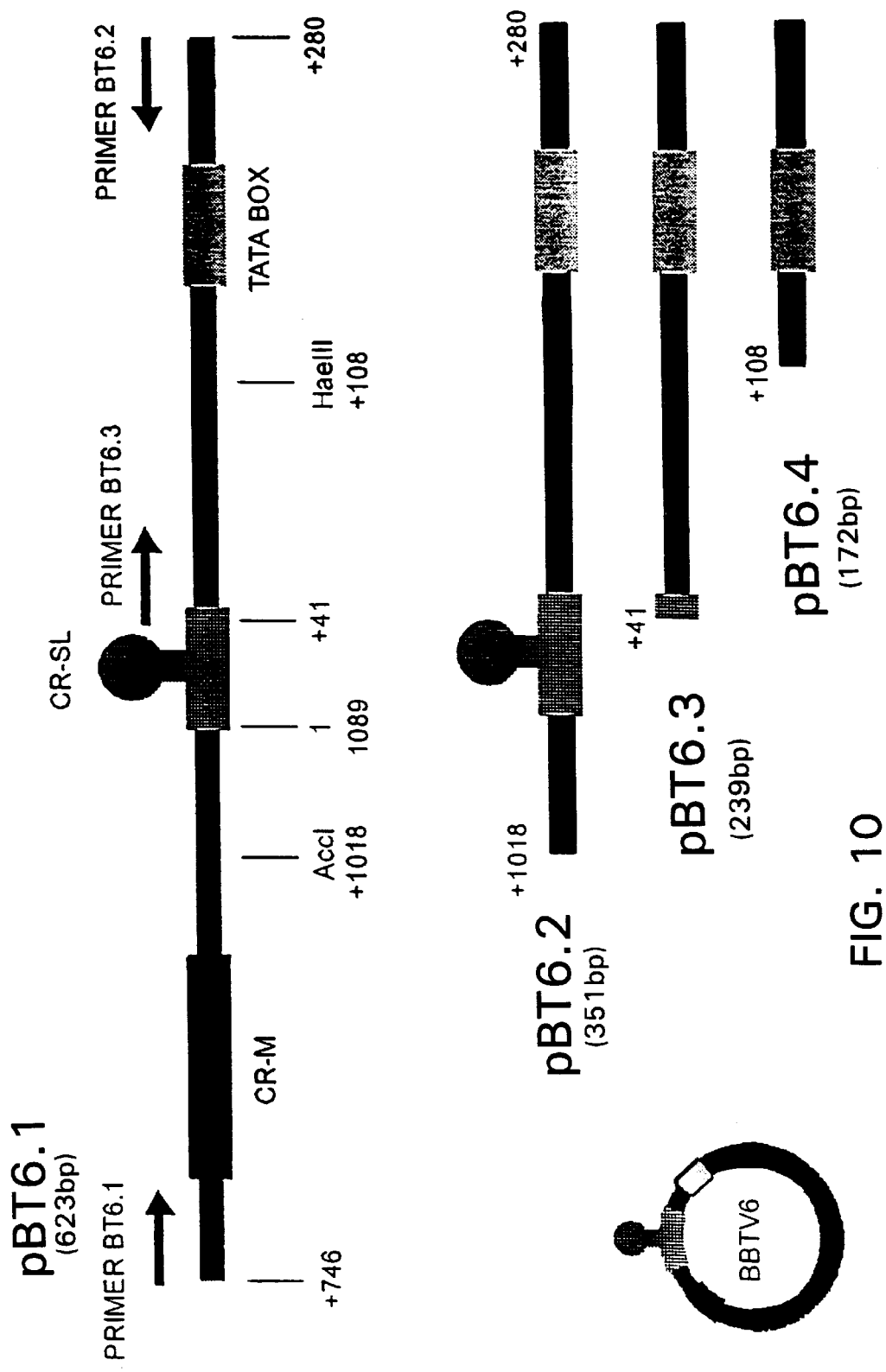
FIG. 10 is a diagrammatic representation of various constructions of the intergenic region of component 6.

Components 3, 4, 5 and 6 all had one large ORF in the virion sense, 3' of the CR-SL. Each of these ORFs had potential conserved TATA boxes and polyadenylation signals associated with them (FIG. 8). The potential TATA boxes highly conserved with the nonanucleotide sequence CTATa/ta/tAa/tA(SEQ ID NO:55) which was essentially similar to that described by Bucher et a., 1990, Journal of Molecular Biology 212 563–578. The distance between the potential TATA box and the translation initiation codon varied in each component from 13 nucleotides in component 3 to 102 nucleotides in component 1. An ATGG translation initiation codon was identified in the five components encoding large ORFs. However, two possible translation initiation codons were identified in component 3, the first at nucleotide 213 (ATGT) and the second at nucleotide 227 (ATGG); the second initiation codon was in frame with the first. This would suggest that the second initiation codon is the correct codon; this could be verified by 5' RACE or N-terminal sequencing of the ORF translation product. GT-rich regions were identified 0 to 24 nucleotides 3' of each of the polyadenylation signals in components 1, 3, 4, 5 and 6. Each of these GT-rich regions contained the nucleotide sequence TTG. Both the polyadenylation signals in components 3 and 6 had these sequences. The combination of a consensus polyadenylation signal (Aa/tTAAa/t) and a 3' proximal GT-rich region containing the trinucleotide sequence TTG were only associated with the single major virion sense ORF in components 1, 3, 4, 5 and 6 and were not identified elsewhere in these sequences suggesting that each of these components encoded a single gene. Similar sequences have been associated with many polyadenylation signals and may be required for efficient termination (Gil & Proudfoot, 1984, Nature 312 473–474; Conway & Wickens, 1985, Proceedings of the National Academy of Sciences U.S.A. 82 3949–3953).

EXAMPLE 2

Modification of Expression With Intergenic Regions of BBTV

Materials and Method

The Plasmids

Agrobacterium-mediated Transformation

All potential promoter sequences derived from the BBTV genome were ligated into the Agrobacterium binary vector, pBI101.3 (Clontech). This plasmid has an antibiotic resistance cassette consisting of nopaline synthase promoter/NPTII gene (kanamycin resistance gene)/nopaline synthase (NOS) terminator and a "promoterless" β-glucuronidase gene (GUS) with a NOS terminator. The BBTV derived sequences were ligated separately into the unique BamHI site 5' of the promoterless GUS gene. The plasmid, pBI121 (Clontech) was used as the control plasmid. This plasmid is identical to pBI101.3 except that it has the CaMV 35S promoter 5' of the GUS gene promoting GUS expression.

Micro-projectile Bombardment

For transient analysis of BBTV promoter activity via micro-projectile bombardment, the BBTV promoter/GUS/nos cassette was sub-cloned into pGEM3zf$^+$ (Promega). As a positive control for most experiments the CaMV 35S promoter/GUS/nos cassette was similarly sub-cloned from pBI121 into pGEM3zf$^+$ (pGEM35S-GUS). Large quantities of these plasmids in a highly purified form were prepared for biolistics using Qiagen Plasmid Maxi Kit (Qiagen) as per manufacturers instructions.

Transformation

The plasmids, pBI121, pBI101.3 or pBI101.3 with BBTV derived sequences 5' of the GUS gene were introduced into a range of plant species and tissue types either by micro-projectile bombardment, electroporation or Agrobacterium-mediated transformation (Horsch et al., 1989, In: Plant Molecular Biology Manual, Gelvin et al. (eds.) Dordrecht Kluwer Academic Publishers, pp A5/1–A5/9; Hauptmann et al., 1987, Plant Cell Reports 6 265–270; Last et al., 1991, Theoretical and Applied Genetics 81 581–588).

Assay for GUS expression is essentially the same as described in Jefferson, 1987, Plant Molecular Reporter 5(4): 387–405.

Preparation of BBTV Promoter Constructs

Primers

| | | |
|---|---|---|
| BT6.1 (25mer) | 5' gcctgcagagttgtgctgtaatgtt 3' | (SEQ ID NO:41) |
| BT6.2 (24mer) | gcggatccgcttctgccttccgct | (SEQ ID NO:42) |
| BT6.3 (25mer) | gccctgcagcatggacgtcagcaagg | (SEQ ID NO:43) |
| BT3.1 (24mer) | gcctgcagactattgtatggaatg | (SEQ ID NO:44) |
| BT3.2 (23mer) | gcggatccctatctagacactgg | (SEQ ID NO:45) |
| BT4.1 (23mer) | gctctagaatgggtattgatgta | (SEQ ID NO:46) |
| BT4.2 (25mer) | gcggatccttagctgcgtcctattt | (SEQ ID NO:47) |
| BT5.2 (23mer) | gcggatccgacgagtgatttcgg | (SEQ ID NO:48) |
| BT129V3.17 (17mer) | gttatcatggcatcgac | (SEQ ID NO:49) |
| BT1R1.17 (17mer) | gaacaagtaatgacttt | (SEQ ID NO:50) |
| BT1.F4.30 (30mer) | ggaagaagcctctcatctgcttcagagagc | (SEQ ID NO:51) |
| BT1.INT.R28 | ggatcctacatgacaatttaaatgaacc | (SEQ ID NO:52) |
| BT1.INT.F25 | aagcttataaaacgaaggcgatgaa | (SEQ ID NO:53) |

PCR Conditions

Sequential Steps 1. 94° C.×5 min 2. 94° C.×1 min)

42° C.×1 min)×40

72° C.×1 min)

3. 72° C.×10 min

1. Cloning of BBTV Intergenic Regions

BBTV Component 6

Full length component six (1089 bp)

1. Intergenic region was PCR amplified from BBTV6 clone P2A1 using primers BT6.1 (+746) and BT6.2 (+280).

2. The 623 bp intergenic region was subcloned as a PstI and BamHI fragment into pUC19 (pUC6.1).

3. The intergenic region was cloned from pUC6.1 as a HindIII and BamHI fragment into pBI101.2 (pBT6.1).

4. The BBTV6 promoter/GUS/nos fragment from pBT6.1 was subcloned into pGEM3zf⁺ as a HindIII and EcoRI fragment (pGEM6.1-GUS).

Generation of BBTV6 Intergenic Region 5' Deletions

Construction of pBT6.2

1. A 272 bp 5' deletion of the BBTV6 intergenic region was generated by digestion of pUC6.1 with AccI, a restriction site present at +1018 in the component six circle, and PstI present in the 5' region of the multiple cloning site of pUC19.
2. The ends were filled using Klenow fragment and religated to produce pUC6.2.
3. The 351 bp fragment was cloned from pUC6.2 as a HindIII and BamHI fragment into pBI101.3 (pBT6.2).
4. The BBTV6 promoter (351 bp)/GUS/nos cassette was subcloned from pBT6.2 as a HindIII and EcoRI fragment into pGEM3zf⁺ (pGEM6.2-GUS).

Construction of pBT6.3

1. A 384 bp 5' deletion of the BBTV6 intergenic region was generated by PCR amplification from BBTV6 clone P2A1 using primers BT6.3 (+41) and BT6.2 (+280).
2. The 239 bp intergenic region was cloned as a PstI and BamHI fragment into pUC19 (pUC6.3).
3. The intergenic region was cloned from pUC6.3 as a HindIII and BamHI fragment into pBI101.3 (pBT6.3)
4. The BBTV6 promoter (239 bp)/GUS/nos cassette was subcloned from pBT6.3 as a HindIII and EcoRI fragment into pGEM3zf⁺ (pGEM6.3-GUS).

Construction of pBT6.4

1. A 451 bp 5' deletion of the BBT6 intergenic region was generated by digestion of pUC6.3 with BamHI and HaeIII (a restriction site present at position +108 in the BBTV 6 circle).
2. Ends were filled using Klenow fragment and the 172 bp fragment blunt-end cloned into the SmaI site of pBI101.3 (pBT6.4).
3. The BBTV6 promoter (172 bp)/GUS/nos cassette was subcloned from pBT6.4 as a HindIII and EcoRI fragment into pGEM3zf⁺ (pGEM6.4-GUS).

BBTV Component I

Full length component one (1111 bp)

1. A 225 bp fragment containing the BBTV1 intergenic region was PCR amplified from full-length BBTV1 clone using primers BT1R1.17 (+986) and BT1F4.30 (+129).
2. The resulting PCR product was digested with TaqI (a restriction site present at position +118 in the BBTV1 circle).
3. The resulting 214 bp fragment was blunt ended using Klenow fragment and cloned into the SmaI site of pBI101.3 (pBT1.1).
4. The BBTV1 promoter (214 bp)/GUS/nos cassette was subcloned from pBT1.1 as a HindIII and EcoRI fragment into pGEM3zf⁺ (pGEM1.1-GUS).

Note: A small ORF in BBTV-1 was identified by 3' RACE experiments. This ORF is located at position +430 to +565. Based on the location of this ORF another BBTV-1 intergenic promoter was isolated.

1. The large intergenic region based on the recently identified smaller ORF in BBTV-1 was PCR amplified from full length BBTV-1 clone using primers BT1.INT.R28 (+429) and BT1.INT.F25 (+560).
2. The resulting 980 bp intergenic region was cloned upstream of the GUS reporter gene in pBI101.3 as a BamHI and HindIII fragment (pBT1.INT).

BBTV Component 2

Full length component two (1059 bp)

BBTV2 full length double stranded replicative form, cloned into pUC19 as an XbaI fragment at position +361 (pUC-BT2) was obtained from Raktham Wanitchakom.

1. An 855 bp intergenic fragment was generated from pUC-BT2 by digestion with XbaI and AccI (a restriction site present at position +565 in the component two circle). The AccI end was blunt ended using Klenow fragment and the XbaI site kept sticky.
2. This full intergenic region was directionally cloned into similarly prepared pGEM3zf⁺ vector (pGEM2.1).
3. The intergenic region was cloned from pGEM2.1 as a HindIII and BamHI fragment into pBI101.3 (pBT2.1).
4. The BBTV2 promoter (866 bp)/GUS/nos cassette was subcloned from pBT2.1 as a HindIII and EcoRI fragment into pGEM3zf⁺ (pGEM2.1-GUS).

BBTV Component 3

Full length component three (1075 bp)

1 Component 3 full intergenic region was PCR amplified from BBTV infected banana nucleic extract (QId) using primers BT3.1 (+761) and BT3.2 (+212).
2. The 526 bp intergenic region was subcloned as a PstI BamHI fragment into pGEM3zf⁺ (pGEM3.1).
3. The intergenic region was cloned from pGEM3.1 as a HindIII and BamHI fragment into pBI101.3 (pBT3.1).
4. The BBTV3 promoter (526 bp)/GUS/nos cassette was subcloned from pBT3.1 as a HindIII and EcoRI fragment into pGEM3zf⁺ (pGEM3.1-GUS).

BBTV Component 4

Full length component four (1043 bp)

1. Component 4 full intergenic region was PCR amplified from BBTV infected banana nucleic extract (QId) using primers BT4.1 (+662) and BT4.2 (+278).
2. The 659 bp intergenic region was subcloned as an XbaI and BamHI fragment into pGEM3zf⁺ (pGEM4.1).
3. The intergenic region was cloned from pGEM4.1 as an XbaI and BamHI fragment into pBI101.3 (pBT4.1).
4. The BBTV4 promoter (659 bp)/GUS/nos cassette was subcloned from pBT4.1 as an XbaI and EcoRI fragment into pGEM3zf⁺ (pGEM4.1-GUS).

BBTV Component 5

Full length component five (1018 bp)

1. Component 5 full intergenic region was PCR amplified from BBTV diseased banana nucleic acid extract (QId) using primers BT129V3.17 (+639) and BT5.2 (+230).
2. The resulting PCR product was digested with BamHI and AccI (a restriction site present at position +794 in the component 5 circle). The AccI site was blunt ended using Klenow fragment and the BamHI end kept sticky.
3. The resulting 454 bp intergenic region was directionally sub-cloned into similarly prepared pGEM3zf⁺ (pGEM5.1).
4. The intergenic region was cloned from pGEM5.1 as a HindIII and BamHI fragment into pBI101.3 (pBT5.1).
5. The BBTV5 promoter (454 bp)/GUS/nos cassette was subcloned from pBT5.1 as a HindIII and EcoRI fragment into pGEM3zf⁺ (pGEM5.1-GUS).

2. Transient Analysis of BBTV Promoter Activity via Micro-projectile Bombardment of *Nicotiana tabacum* (NT) Cell Line Preparation of NT Cell Suspension 1. 25 mL of NT cell suspension was subcultured into 75 mL of fresh NT liquid media and shaken at 28° C. under moderate light
2. Two days post subculture, 50 mL of the actively growing NT culture was transferred to a 50 mL Falcon tube and allowed to settle for 5–10 min.
3. The resulting packed NT cell volume was resuspended in an equal volume of NT liquid media.
4. 200 μL aliquots of the NT cell mix were spotted onto NT solid media and allowed to air dry for 3–4 hrs.

5. NT spots were incubated at 28° C. under moderate light for 2 days.

6. NT spots were subjected to micro-projectile bombardment as described below. Five NT spots were shot per promoter construct.

7. Following biolistics NT spots were incubated at 28° C. under moderate light for 3 days.

8. Promoter activity was qualitatively analysed by GUS staining one NT spot per promoter construct using X-glucuronide substrate. The remaining four NT spots were subjected to quantitative GUS fluorometric analysis using MUG substrate. These techniques were performed essentially as described Jefferson, 1987, Plant Molecular Reporter 5(4): 387–405.

Preparation of DNA-gold Suspension for Micro-projectile Bombardment

1. Gold suspension was vortexed briefly and sonicated in ice water for 30 sec.

2. DNA-gold suspension was prepared on ice by addition of 2 μg of DNA, 25 μL of CaCl.2H$_2$O (2.5M) and 5 μL of spermidine free base (0.1M) to 25 μL of gold suspension (100 mg/mL).

3. DNA-gold suspension was vortexed intermittently for 5 min then left to settle on ice for 10 min.

4. A 22 μL volume of the supernatant was removed and discarded. The remaining suspension was vortexed and a 5 μL aliquot used for micro-projectile bombardment.

5. One preparation of gold was used per promoter construct. This DNA-gold suspension provided enough suspension to shoot five NT spots.

Shooting Conditions for the Particle Inflow Gun 25 mm Hg vacuum

Helium pressure approximately 550 Kpa

Platform height 10 cm

Mesh used to protect target

Constructs Used

Tests: pGEM6.1-GUS, pGEM6.2-GUS, pGEM 6.3-GUS, pGEM6.4-GUS pGEM1.1-GUS, pGEM2.1-GUS, pGEM3.1-GUS, pGEM4.1-GUS, pGEM5.1 -GUS Controls: pGEM35S-GUS Results: The results of the experiment are shown in FIG./

Comparison of BSTV6 Promoter Activity

1. The full intergenic region of BBTV component six has promoter activity comparable to that of the 800 bp CaMV 35S promoter from pBI121.

2. The 272 bp 5' deletion (pGEM6.2-GUS) causes a significant increase in promoter activity which is maintained with a further 112 bp 5' deletion (pGEM6.3-GUS).

3. Promoter activity is significantly reduced with a further 75 bp 5' deletion (pGEM6.4-GUS).

Significance of Results

The increase observed in promoter activity between plasmids pGEM6.1-GUS and pGEM6.2-GUS implies the 272 bp region surrounding the CR-M may contain a putative down-regulatory sequence responsible for this reduction in promoter activity.

The levels of promoter activity observed between plasmids pGEM6.2-GUS, pGEM6.3-GUS and pGEM6.4-GUS indicates the majority of the strong promoter activity associated with the BBTV6 intergenic region is associated with a 112 bp region situated 3' of the CR-S/L. Importantly, this region contains a putative promoter motif TGA-1b (position +44), which contains the core sequence TGACGT, analogous to other promoter motifs and transcription factor binding domains.

Comparison of BBTV1–6 Promoters

1. BBTV-1 promoter has no activity in transient transformation of NT cell suspensions.

2. BBTV-2 promoter has the highest promoter activity of the six BBTV components, with levels 2–3 fold greater than the 800 bp CaMV 35S promoter derived from pBI121.

3. BBTV-3, -4, and -5 promoters are relatively weak with levels of activity about 50% less than the CaMV 35S promoter.

4. BBTV-6 full intergenic region has similar level of promoter activity as that of the CaMV 35S promoter.

Significance of Results

The absence of promoter activity associated with the BBTV-intergenic region may indicate this promoter has a highly tissue specific expression pattern or requires transcription factors absent in tobacco nuclei. The identification of a putative promoter motif (Type-1 element of the wheat histone H3 gene) associated with S-phase specific cell expression within this promoter may imply its activity is restricted to actively dividing meristematic tissue types.

The high levels of promoter activity associated with the BBTV-2 intergenic region may make this sequence a potentially useful promoter to drive high level expression. Despite the fact that BBTV infects a monocot, it appears from this study BBTV2–6 promoters are active, to varying degrees, in a dicot system.

3. Transient Analysis of BBTV Promoter Activity in Other Plant Species

Micro-projectile Bombardment of Cucumber

1. Cucumber pre-embryogenic callus was sub-cultured onto SQM2EV media 2 weeks prior to biolistic transformation.

2. Callus was transferred to small SQM2EV plates 4 days prior to biolistic transformation.

3. Micro-projectile bombardment was done as previously above.

4. GUS activity was observed in transformed callus via qualitative GUS staining using X-glucuronide substrate (2 days post biolistics).

Constructs Used: pBT6.1, pBT6.3, pBT1.1, pBI121

Results

1. Both pBT6.1 and pBT6.3 produced a similar number of blue foci (transformation events) as pBI121 following GUS staining.

2. pBT1.1 showed no evidence of promoter activity in cucumber callus (ie. no blue foci were observed).

Electroporation of Zucchini Protoplasts

Isolation of Zucchini Protoplasts

1. A 1.5 mL volume of embryogenic zucchini callus suspension was mixed with 20 mL of Enzyme Mix (E3) and incubated at 25° C. in the dark on a slow shaker (30–50 RPM) for 5–6 hrs.

2. Protoplasts were isolated by passage through 450 μm, 105 μm and 51 μm sized sieves and centrifugation at 40–50 9 for 5 min.

3. Proplasts were washed once in PWS solution and finally resuspended in a known volume of TBS.

4. Cell numbers were estimated using a calibrated slide counter and the volume adjusted to contain 1×10$^6$ protoplasts/mL.

5. 10 μg of plasmid DNA was added to 1 mL of protoplasts and incubated on ice for 10 min.

Electroporation of Zucchini Protoplasts

1. The protoplasts: DNA mixture was electroporated in a BioRad electroporation cuvette (0.4 cm electrode gap) with 10 μg of plasmid DNA using a Gene Pulsar (BioRad) apparatus with 3 pulses of 300V, 10 msec pulse width and 100 msec pulse delay.

2. Protoplasts were incubated for a further 10 min on ice and pelleted by centrifugation at 1000 RPM in a microfuge.

3. Protoplasts were washed once in Culture Media 415A and finally resuspended in 1 mL of 415A.

4. Protoplasts were transferred to a 12 well microtitre plate and incubated for 48 hrs on a slow shaker in the dark.

5. Following incubation the protoplasts were harvested by centrifugation and assayed for GUS activity.

Fluorometric GUS Assay

1. A 5 µg quantity of extracted protoplast protein was used standardly for fluorometric assays (estimated using BioRad Protein Assay Reagent).

2. Volume was adjusted to 100 µL with protein extraction buffer and incubated with 100 µL of MUG substrate (2 mM) at 37° C. for 30 min.

3. Reactions were stopped by addition of 1 mL of $Na_2CO_3$.

4. Enzymic activity was estimated against a 4-MU standard curve (0–500 nM) using a fluorometric spectrophotometer (excitation—365 nm; emission—455 nm; integration time—10).

The GUS activity was analysed using a fluorometric assay described by Jefferson, 1987, Plant Molecular Reporter 5(4): 387–405. Constructs Used: pBT6.3, pBT1.1, pBI121.

Results

| CONSTRUCT | GUS ACTIVITY (pmol MU/min/mg protein) |
| --- | --- |
| pBI101.3 | 0 |
| pBI121 | 10,000 |
| pBT1.1 | <1000 |
| pBT6.3 | 22,000 |

No GUS activity was observed with the promoterless GUS binary vector (pBI101.3)

Levels of GUS activity driven by the 239 bp fragment of BBTV6 intergenic region (pBT6.3) were 2-fold greater than the 800 bp CaMV 35S promoter (pBI121)

Little to no GUS activity was observed from the BBTV1 promoter (pBT1.1).

Micro-projectile Bombardment of Wheat Cell Suspension

1. Wheat cell suspension was subcultured into 50 mL WTL1 media 4 days prior to micro-projectile bombardment.

2. Wheat cells were pelleted by low speed centrifugation and resuspended in 10 mL WTL1 media.

3. Cells were transferred to sterile filter paper immediately prior to bombardment.

4. Micro-projectile bombardment was done as previously described.

5. Two days post-biolistics the transformed wheat suspension was subjected to GUS staining using X-glucuronide substrate.

Constructs Used: pBT1.1, pBT2.1, pBT3.1, pBT4.1, pBT5.1, pBT6.1, pBI121, DM8052 (rice actin enhanced promoter driving GUS expression).

Results

1. Rice actin enhanced promoter produced >5000 blue foci per transformation.

2. pBI121 produced, on average approximately 70 blue foci per transformation.

3. Of all the BBTV promoter constructs tested, only pBT2.1 was active, producing on average 100 blue foci per transformation.

Micro-projectile Bombardment of Banana Male Flower Embryogenic Callus

1. An embryogenic culture of Cavendish banana cv. "Williams" was generated using male flowers as described by Escalant et al., 1994, In Vitro Cellular and Developmental Biology 30P: 181–186. This culture was maintained in a temporary immersion system in liquid MP medium (Escalant et al., 1994, In Vitro Cellular and Developmental Biology 30P: 181–186).

2. Five days prior to micro-projectile bombardment the embryogenic callus was transferred to solid MP medium.

3. Tissue was subjected to micro-projectile bombardment as previously described.

4. Transient GUS activity was visualised by GUS staining using X-glucuronide substrate 2 days post biolistics.

Constructs Used: pGEM2.1-GUS, pGEM3.1-GUS, pGEM4.1-GUS, pGEM5.1-GUS, pGEM-Ubi (Maize ubiquitin promoter driving GUS expression).

Results

1. Maize ubiquitin promoter drives high level expression of GUS in this tissue type, with intensely blue staining foci or transformation events (the exact number of foci are difficult to determine due to intensity and number).

2. Of the BBTV promoter constructs tested, all promoters have shown low levels of activity (<10 blue foci per transformation). The approximate order of strength based on the number of blue foci is: pGEM2.1-GUS (highest), pGEM4.1-GUS, pGEM3.1-GUS, and pGEM5.1-GUS (lowest).

Significance of Results

Results from transient analysis of BBTV promoter activity in alternative plant species indicate that the BBTV6 promoter (particularly the 239 bp fragment, pBT6.3) appears to be active in undifferentiated cucurbit (dicot) tissue types.

Results from micro-projectile bombardment of wheat cell suspension imply only the BBTV2 promoter is active to a significant degree. This result indicates that at least one of the BBTV promoters is active to some extent in Graminaceae monocots.

Transient assays using banana embryogenic cultures indicates that the BBTV promoters tested to date have some level of activity in their host plant species. Again, the strongest of the BBTV promoters tested was that of BBTV component 2, which may reflect its importance as a potentially useful promoter in the future.

4. Stable Transformation of NT Cell Suspension by Agrobacterium Infection

1. Two to three days prior to transformation a 5 mL LB culture containing 100 µ/mL kanamycin was inoculated with the transformed Agrobacterium strain of interest, from 40% glycerol stock.

2. NT cells were used 5–7 days post-subculture (4 mL of this culture was used per transformation, with an additional 4 mL for the control which received no bacteria). Note: duplicate transformation were performed for each construct.

3. 1 µL of acetosyringone (2 mM in ethanol) was added per mL of NT cells.

4. Using a 5 mL pipette, the NT cells were pipetted in and out about 20 times to help induce lesions and enhance the transformation event.

5. 100 µL of Agrobacterium culture (dense growth) was added to a microtitre plate containing 4 mL of the treated NT cells, and mixed thoroughly.

6. Plates were incubated for 3 days at 28° C. under moderate light.

7. Post incubation, 10 mL of NT liquid medium containing 500 µg/mL carbenicillin (NTC) was added to each well.

8. Cells were centrifuged at 1K for 4 min in 5 mL Falcon tubes made up to volume with NTC.

9. Washes were repeated 2 times.

10. Cells were finally resuspended in 5 mL NTC and 2 mL plated onto 2 NTKC solid media (kanamycin 100 µg/mL, carbenicillin 500 μg/mL). Plates were incubated at 28° C. under moderate light.

11. 3–4 weeks post infection transformants were subcultured individually and maintained under selection with fortnightly subculturing.

12. Promoter activity was observed by GUS staining using X-glucuronide substrate.

Constructs Used: pBT6.1 (3 NT lines), pBT6.2 (3 NT lines), pBT6.3 (2 NT lines), pBT2.1 (25 NT lines).

Results

1. Strong GUS activity in stably transformed NT callus with all BBTV promoter constructs.

2. Some variation in expression between different lines of BT2.1 transformed NT, most probably due to the position effect (position of DNA integration into host genome) and number of integrated copies.

Significance of Results

These experiments indicate that the BBTV6 and BBTV2 promoters are highly active in stably transformed tobacco undifferentiated cell types. These findings support results from micro-projectile bombardment, in which these promoters showed strong transient activity. Furthermore, these results confirm that activity from these promoters is not affected to a significant degree by stable integration in the host genome.

5. Stable Transformation of Tobacco by Agrobacterium-mediated Infection of Leaf Discs 1. Promoter binary constructs were introduced into Agrobacterium strain LBA4404 by electroporation.

2. Transformed Agrobacterium were grown under kanamycin selection (100 μg/mL) and confirmed to contain the promoter construct by a modified alkaline lysis procedure.

3. Two to three days prior to transformation a 5 mL LB culture of the transformed Agrobacteria to be used was initiated from either a single colony or 40% glycerol stock, and shaken at 28° C.

4 The culture was diluted 1 in 20 with LB and transferred to a sterile 10 mL vial.

5. Leaves from 3–6 week old tobacco (Nicotiana xanthii) were excised and cut into pieces 1 cm×1 cm.

6. These pieces were transferred to the diluted Agrobacterium culture and left to soak for 10–15 min.

7. Tobacco pieces were blotted dry on sterile filter paper, placed adaxial (upper) side down on MS104 medium and incubated at 28° C. until a slight bacterial growth was visible (2–3 days).

8. Leaf pieces were transferred to MS104 selection media (100 mL kμg/anamycin and 200 μg/mL timentin), and incubated under moderate light at 28° C.

9. After approximately 2 weeks crown gall callus was visible at the site of infection. After a further 2–5 weeks shoots were apparent.

10. When well defined stems were visible, shoots were excised and placed in MS Rooting Media (100 μg/mL kanamycin and 200 μg/mL timentin).

11. Actively growing plantlets (with root systems) were maintained in culture under selection and putative transformants subjected to qualitative GUS staining using X-glucuronide substrate.

12. In general 6–12 putative transformants were obtained per promoter construct.

Constructs used

Tests: pBT6.1, pBT6.2, pBT6.3, pBT6.4 pBT2.1, pBT2.2, pBT2.3, pBT2.4 pBT1.1, pBT3.1, pBT4.1, pBT5.1

Controls: pBI121

Results

1. Strong constitutive GUS expression in leaves, stems, and roots transformed with pBI121.

2. Weak phloem-limited GUS expression in leaf and root sections from about 10% of tobacco plantlets transformed with the BBTV promoter constructs. The remaining 90% of transformants displayed no GUS activity within leaves and roots.

Significance of Results

Results obtained from qualitative GUS staining of tissue from the majority (90%) of tobacco stably transformed with the BBTV promoter constructs, implies these promoters have little to no promoter activity in whole plants or differentiated tissues. The fact that some BBTV intergenic regions (components 2 and 6) show high levels of expression in transient systems (micro-projectile bombardment of *Nicotiana tabacum* cell line), indicates the activity of these promoters may be limited to undifferentiated cell types, or that these promoters are silenced in the transition from undifferentiated callus to differentiated cell types. This theory is further supported by experiments in which callus regenerated from leaves of stably transformed tobacco (showing no GUS activity) display varying levels of GUS expression upon staining.

The benefit of such a unique expression pattern may be in driving selective resistance, as most plant transformation systems rely on strong selection of transformed tissue during an undifferentiated cell phase. Therefore a transformation cassette containing a BBTV promoter (component 2 or 6) driving NPTII expression would provide strong kanamycin resistance in transformed tissue during the early stages of plant transformation (callus phase), but once cells were differentiated (ie. formation of shoots, leaves, etc.) the promoter would be switched off. As the expression of antibiotic and herbicidal selection genes in transgenic plants is a major concern in certain countries, the use of such a promoter would be beneficial.

6. Analysis of BBTV Promoter Driving NPTII Expression

Generation of BBTV6-NPTII Construct

1. The 239 bp fragment of BBTV component 6 intergenic region from pUC6.3 was cloned upstream of the 800 bp NPTII gene with CaMV 35S terminator as a BamHI and PstI fragment.

2 The resulting BBTV6 promoter (239 bp)/NPTII/CaMV 35S terminator cassette was subcloned as a SacI and XbaI fragment between the left and right borders of the Agrobacterium T-DNA in the binary vector pTAB5.

Figure 14:
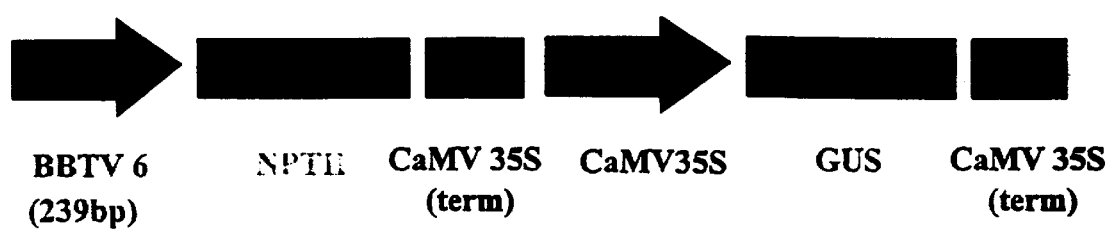
FIG. 14 is a representation of the BBTV6-NPTII construct.

3. The CaMV 35S promoter (530 bp)/GUS/CaMV 35S terminator (200 bp) cassette from pGUS2 was cloned downstream as an EcoRI fragment (see FIG. 14).

4. The resulting vector pBT6.3-NPT detailed below was subsequently used for Agrobacterium-mediated transformation of tobacco (as previously described).

Analysis of Transformants

1. Eight putative transformants were obtained following Agrobacterium-mediated transformation of tobacco (*Nicotiana xanthii*) with the pBT6.3-NPT construct. These eight plants were selected in media containing kanamycin at a concentration of 100 μg/mL.

2. Levels of NPTII expression from these plants were estimated using a quantitative NPTII ELISA Kit (5 Prime- 3 Prime) as per manufacturers instructions. Comparisons were made between tissue types (leaves and roots) and between promoters (CaMV 35S promoter and nopaline synthase promoter).

Results

The results of experiments are shown in FIG. /

1. High levels of NPTII expression were obtained in both leaves and roots of plants containing the CaMV 35S promoter driving NPTII expression.

2. In general, NPTII levels in the eight plants expressing NPT under the control of the BBTV6 promoter were significantly lower than CaMV 35S promoter. Levels of NPTII expression in the leaves did not exceed 6 ng NPTII/mg protein. Levels within the roots were slightly higher but did not exceed 12 ng NPTII/mg protein. These levels of expression are comparable with the nos promoter.

Significance of Results

These experiments have shown that the 239 bp fragment of the BBTV6 intergenic region is capable of driving selective resistance in stably transformed tobacco. As predicted, the levels of NPTII expression in the stably transformed plants (leaves and roots) were very low, but comparable with that of the nopaline synthase promoter.

7. Regulatory Elements Present in the BBTV Intergenic Regions (I) TATA box present in all BBTV components and positioned upstream of the transcriptional start codon conserved nonanucleotide sequence CTATa/ta/tAa/tA (SEQ ID NO:55)

responsible for the correct initiation of transcription (ii) TGA1-a motif consensus sequence TGACGTAA(SEQ ID NO:56)

as-1 binding motif involved in transcription regulation (iii) TGA1-b motif hexamer binding motif with consensus sequence TGACGT(SEQ ID NO:57)

(iv) Promoter type 1 element of wheat histone H3 gene (hexamer motif)

consensus sequence ACGTAA(SEQ ID NO:58)

present immediately 3' of the CR-S/L in all BBTV components hexamer motif binds related TAF-1 and HBP-1 proteins linked to expression specifically in the S-phase of the cell cycle (Nakayama et al., 1992, FEBS Letters, 300: 167–170) suggesting promoter activity is limited to undifferentiated, actively dividing cells (v) Adh1 US1 consensus sequence CCACG(SEQ ID NO:59)

binding factor unknown present in all BBTV intergenic regions (either in virion or complementary sense)

(vi) Adh1-US3 consensus sequence CGTGG(SEQ ID NO:60)

binding factor unknown present in all BBTV intergenic regions (either in virion or complementary sense)

8. Plant Tissue Culture Solutions and Media

| MSO Medium | NT Solid Media |
|---|---|
| MS Salts | NT liquid media |
| myo-inositol 100 μg/mL | TC Agar 0.7% |
| thiamine-HCl 10 μg/mL | |
| nicotinic acid 1 μg/mL | |
| pyridoxine-HCl 1 μg/mL | |
| sucrose 3% | |
| TC agar 0.7% | |
| pH 5.7 | |

| -continued | |
|---|---|
| MS104 Medium | NTC Media |
| MSO | NT liquid media |
| benzyladenine 1 μg/mL | carbenicillin 500 μg/mL |
| naphthaleneacetic acid 0.1 μg/mL | |
| pH 5.7 | |
| MS Selection Media | NTKC Media |
| MS104 | NT solid media |
| kanamycin 100 μg/mL | kanamycin 100 μg/mL |
| timentin 200 μg/mL | carbenicillin 500 μg/mL |
| MS Rooting Media | SQM2EV Media |
| MSO with 0.6% TC ager | MS Salts |
| kanamycin 100 μg/mL | Myo-inositol 1 mg/mL |
| timentin 200 μg/mL | sucrose 3% |
| | TC Agar 0.7% |
| | 2,4-D 10 μM |
| | BAP 1.5 μM |
| NT Liquid Media | WTL1 Media |
| MS Salts | MS Salts |
| Sucrose 3% | CAB A organics |
| MES 0.5 μg/mL | L-asparagine 5 μg/mL |
| B1-Inositol 1 μg/mL | L-glycine 10 μg/mL |
| KH$_2$PO$_4$ 180 μg/mL | Gibco coconut water 2% |
| 2,4-D 0.222 μg/mL | NZ amine 50 μg/mL |
| pH 5.7 | glucose 10 mg/mL |
| | sucrose 20 mg/mL |
| | mannitol 20 mg/mL |
| | 2,4-D 2 μg/mL |
| | kinetin 0.2 μg/mL |
| | pH 5.8 |

PWS Solution—(1 Liter)

| calcium chloride | 735 mg |
|---|---|
| MES | 639.6 mg |
| mannitol | 109.3 g |
| pH 5.6 | |

Enzyme Mix (E3)

2.0% cellulase (R-10)

0.5% macerozyme (R-10)

0.5% hemicellulase 1.0% pectolyase (Y23)

0.5% BSA

Made up to volume with PWS (pH5.6)

TBS SOLUTION—(200 mL)

| Trizma base | 0.73 g |
|---|---|
| sodium chloride | 1.75 g |
| calcium chloride | 0.18 g |
| mannitol | 9.2 g |
| pH 9.0 | |

9. Significance of the CR-M

DNA sequence alignments of the BBTV components 1–6 CR-M are supplied. This region is thought to act as a putative primer binding site and suggested to play a role in BBTV replication. Although the CR-M of BBTV contains two direct GC-repeats which resemble the Sp1 binding sites found in the promoters of genes in animals and viruses (eg. maize streak virus) it appears this region has no promoter enhancing role. This hypothesis is supported by 5' deletion analysis of the BBTV6 intergenic region which has demonstrated that removal of a 272 bp region including the CR-M produces a significant increase in promoter activity. Furthermore preliminary studies with the BBTV2 intergenic region have shown no decrease in promoter activity with removal of the CR-M.

CONCLUSIONS

We have demonstrated that the intergenic regions or DNA sequences of BBTV components 1 to 6 have promoter activity and that this activity varies from one intergenic region to another. Using transient and stable expression systems we have shown that the BBTV promoters appear to possess a tissue specific expression pattern which may be analogous to the site of BBTV replication and accumulation in its natural host. Furthermore we have identified potential regulatory elements present in at least one of the BBTV promoters (component 6) which appear to influence reporter gene expression.

BBTV is a virus that infects monocots of the genus Musa. It could be expected therefore that the promoters derived from BBTV would have the strongest activity in banana and potentially other monocots. Transient studies with wheat cell suspensions and banana embryogenic callus have shown some of the BBTV promoters are active to some extent in such systems. Importantly, we have also found that two of the BBTV promoters (BBTV2 and 6) drive high level transient expression in dicotyledonous (tobacco, cucumber, and zucchini) undifferentiated tissue types.

What is claimed is:

1. A recombinant DNA molecule comprising a promoter which comprises the nucleotide sequence of SEQ ID NO:22, SEQ ID NO:23, SEQ ID NO:24, SEQ ID NO:25, SEQ ID NO:26, SEQ ID NO:27, SEQ ID NO:29, SEQ ID NO:30, or SEQ ID NO:31.

2. The recombinant DNA molecule as claimed in claim 1, further comprising a non-BBTV gene operably linked downstream of the promoter.

3. A method of expressing a non-BBTV gene in a plant cell, the method comprising:

obtaining a recombinant DNA molecule which comprises:

(1) a promoter comprising the nucleotide sequence of SEQ ID NO:22, SEQ ID NO:23, SEQ ID NO:24, SEQ ID NO:25, SEQ ID NO:26, SEQ ID NO:27, SEQ ID NO:29, SEQ ID NO:30, or SEQ ID NO:31; and (2) a non-BBTV gene operably linked downstream of the promoter; and introducing the recombinant DNA molecule into a plant cell, wherein the non-BBTV gene is expressed in the plant cell.

4. A transformed plant cell comprising a recombinant DNA molecule comprising a promoter which comprises the nucleotide sequence of SEQ ID NO:22, SEQ ID NO:23, SEQ ID NO:24, SEQ ID NO:25, SEQ ID NO:26, SEQ ID NO:27, SEQ ID NO:29, SEQ ID NO:30, or SEQ ID NO:31.

5. The transformed plant cell as claimed in claim 4, wherein the recombinant DNA molecule further comprises a non-BBTV gene operably linked downstream of the promoter.

6. A transgenic plant comprising a plant cell which comprises a recombinant DNA molecule comprising:

(1) a promoter comprising the nucleotide sequence of SEQ ID NO:22, SEQ ID NO:23, SEQ ID NO:24, SEQ ID NO:25, SEQ ID NO:26, SEQ ID NO:27, SEQ ID NO:29, SEQ ID NO:30, or SEQ ID NO:31; and (2) a non-BBTV gene operably linked downstream of the promoter.

7. The transgenic plant as claimed in claim 6, wherein the nucleotide sequence is SEQ ID NO:22, SEQ ID NO:23, SEQ ID NO:24, SEQ ID NO:25, or SEQ ID NO:26, and the plant is a monocotyledon plant.

8. The transgenic plant as claimed in claim 6, wherein the nucleotide sequence is SEQ ID NO:23, and the plant is a monocotyledon plant.

9. The transgenic plant as claimed in claim 6, wherein the plant is a dicotyledon plant.

10. The transgenic plant as claimed in claim 6, wherein the nucleotide sequence is SEQ ID NO:27, SEQ ID NO:29, SEQ ID NO:30, or SEQ ID NO:31, and the plant is a dicotyledon plant.

11. The transgenic plant is claimed in claim 6, wherein the nucleotide sequence is SEQ ID NO:27, SEQ ID NO:29, SEQ ID NO:30, or SEQ ID NO:31, and the plant is a dicotyledon plant, and the plant cell is in an undifferentiated tissue of said plant.

* * * * *